US010319561B2

(12) United States Patent
Biberger et al.

(10) Patent No.: US 10,319,561 B2
(45) Date of Patent: Jun. 11, 2019

(54) OBJECT PREPARATION DEVICE AND PARTICLE BEAM DEVICE WITH AN OBJECT PREPARATION DEVICE AND METHOD FOR OPERATING THE PARTICLE BEAM DEVICE

(71) Applicant: Carl Zeiss Microscopy GmbH, Jena (DE)

(72) Inventors: Josef Biberger, Wildenberg (DE); Andreas Schmaunz, Oberkochen (DE); Gero Walter, Westhausen (DE)

(73) Assignee: CARL ZEISS MICROSCOPY GMBH, Jena (DE)

( * ) Notice: Subject to any disclaimer, the term of this patent is extended or adjusted under 35 U.S.C. 154(b) by 0 days.

(21) Appl. No.: 15/906,031

(22) Filed: Feb. 27, 2018

(65) Prior Publication Data
US 2019/0103249 A1    Apr. 4, 2019

(30) Foreign Application Priority Data

Mar. 4, 2017  (DE) .................. 10 2017 203 554

(51) Int. Cl.
*H01J 37/20* (2006.01)
*H01J 37/28* (2006.01)
(Continued)

(52) U.S. Cl.
CPC .......... *H01J 37/28* (2013.01); *G01N 23/2252* (2013.01); *G01N 23/2254* (2013.01);
(Continued)

(58) Field of Classification Search
CPC .......... H01J 37/28; H01J 37/153; H01J 37/20; H01J 37/222; H01J 37/224;
(Continued)

(56) References Cited

U.S. PATENT DOCUMENTS 3,872,759 A    3/1975  Jackson
7,193,220 B1 *  3/2007  Navarro .................. G01T 1/169
                                          250/252.1
(Continued)

FOREIGN PATENT DOCUMENTS

DE       2 411 535       9/1974
DE    196 06 969 C2      8/1997
(Continued)

*Primary Examiner* — Nicole M Ippolito
(74) *Attorney, Agent, or Firm* — Muirhead and Saturnelli, LLC

(57) ABSTRACT

An object preparation device for preparing an object in a particle beam apparatus includes at least one cutting device, at least one cutting bevel for cutting the object, where the cutting bevel is arranged at the cutting device, at least one movably embodied object receptacle device having an object receptacle for receiving the object, and at least one drive unit for moving the object receptacle device from a first position of the object receptacle device into a second position of the object receptacle device. The first position of the object receptacle device is an initial position. The second position of the object receptacle device is an analysis and/or processing position of the object receptacle device. An observation axis (OA) extends through the object receptacle when the object receptacle device is arranged at the second position.

25 Claims, 11 Drawing Sheets

(51) Int. Cl.
*G21K 5/04* (2006.01)
*G01N 23/2252* (2018.01)
*G01N 23/2254* (2018.01)
*H01J 37/244* (2006.01)
*H01J 37/153* (2006.01)
*H01J 37/22* (2006.01)

(52) U.S. Cl.
CPC ............ *H01J 37/153* (2013.01); *H01J 37/20* (2013.01); *H01J 37/222* (2013.01); *H01J 37/244* (2013.01); *G01N 2223/418* (2013.01); *H01J 2237/20214* (2013.01); *H01J 2237/221* (2013.01); *H01J 2237/226* (2013.01)

(58) Field of Classification Search
CPC ....... H01J 2237/20214; H01J 2237/221; H01J 2237/226; G01N 23/2252; G01N 23/2254; G01N 2223/418
USPC ............. 250/306, 307, 309, 310, 311, 492.1, 250/492.2, 492.21, 492.22, 492.23, 492.3
See application file for complete search history.

(56) References Cited

U.S. PATENT DOCUMENTS

| | | | |
|---|---|---|---|
| 7,806,983 B2* | 10/2010 | Chiang | C23C 16/0227 118/724 |
| 2004/0036031 A1 | 2/2004 | Rose et al. | |
| 2004/0261597 A1 | 12/2004 | Thiem et al. | |
| 2006/0098184 A1* | 5/2006 | Shibazaki | G03F 7/707 355/75 |
| 2007/0020918 A1* | 1/2007 | Hirokawa | B23H 5/08 438/626 |
| 2013/0140459 A1 | 6/2013 | Galloway | |
| 2014/0092230 A1 | 4/2014 | Langer et al. | |
| 2017/0330724 A1 | 11/2017 | Okumura et al. | |

FOREIGN PATENT DOCUMENTS

| | | |
|---|---|---|
| DE | 10 2004 004 355 B3 | 1/2005 |
| DE | 10 2012 217 761 A1 | 4/2014 |
| DE | 11 2015 004 746 T5 | 8/2017 |
| WO | WO 2002/067286 A2 | 8/2002 |
| WO | WO 2008/066846 A2 | 6/2008 |
| WO | WO 2015/175525 A1 | 11/2015 |

* cited by examiner

OBJECT PREPARATION DEVICE AND PARTICLE BEAM DEVICE WITH AN OBJECT PREPARATION DEVICE AND METHOD FOR OPERATING THE PARTICLE BEAM DEVICE

TECHNICAL FIELD

The system described herein relates to an object preparation device for preparing an object in a particle beam apparatus, such as an electron beam apparatus and/or an ion beam apparatus. The system described herein moreover relates to a particle beam apparatus having such an object preparation device and to a method for operating the particle beam apparatus.

BACKGROUND OF THE INVENTION

Electron beam apparatuses, in particular a scanning electron microscope (also referred to as SEM below) and/or a transmission electron microscope (also referred to as TEM below), are used to examine objects (also referred to as specimens) in order to obtain knowledge in respect of the properties and behaviors of the objects under certain conditions.

In an SEM, an electron beam (also referred to as primary electron beam below) is generated by means of a beam generator and focused on an object to be examined by way of a beam-guiding system. An objective lens is used for focusing purposes. The primary electron beam is guided in a grid-shaped manner over a surface of the object to be examined by way of a deflection device. Here, the electrons of the primary electron beam interact with the object to be examined. In particular interaction particles and/or interaction radiation is/are generated as a result of the interaction. By way of example, the interaction particles are electrons. In particular, electrons are emitted by the object—the so-called secondary electrons—and electrons of the primary electron beam are scattered back—the so-called backscattered electrons. The interaction particles form the so-called secondary beam and they are detected by at least one particle detector. The particle detector generates detection signals which are used to generate an image of the object. An imaging of the object to be examined is thus obtained.

By way of example, the interaction radiation is x-ray radiation or cathodoluminescence. It is detected for example with a radiation detector and is used in particular for examining the material composition of the object.

In the case of a TEM, a primary electron beam is likewise generated by means of a beam generator and focused on an object to be examined by means of a beam-guiding system. The primary electron beam passes through the object to be examined. When the primary electron beam passes through the object to be examined, the electrons of the primary electron beam interact with the material of the object to be examined. The electrons passing through the object to be examined are imaged onto a luminescent screen or onto a detector—for example in the form of a camera—by a system comprising an objective. By way of example, the aforementioned system additionally also comprises a projection lens. Here, imaging may also take place in the scanning mode of a TEM. As a rule, such a TEM is referred to as STEM. Additionally, provision can be made for detecting electrons scattered back at the object to be examined and/or secondary electrons emitted by the object to be examined by means of a further detector in order to image an object to be examined.

The integration of the function of a STEM and an SEM in a single particle beam apparatus is known. It is therefore possible to carry out examinations of objects with an SEM function and/or with a STEM function using this particle beam apparatus.

Furthermore, the prior art has disclosed the practice of analyzing and/or processing an object in a particle beam apparatus using, on the one hand, electrons and, on the other hand, ions. By way of example, an electron beam column having the function of an SEM is arranged at the particle beam apparatus. Additionally, an ion beam column is arranged at the particle beam apparatus. Ions used for processing an object are generated by means of an ion beam generator arranged in the ion beam column. By way of example, material of the object is ablated, or material is applied onto the object during the processing. The ions are used, additionally or alternatively, for imaging. The electron beam column with the SEM function serves, in particular, for examining further the processed or unprocessed object, but also for processing the object.

The aforementioned particle beam apparatuses of the prior art each have a specimen chamber in which an object that is to be analyzed and/or processed is arranged on a specimen stage. It is furthermore known to arrange a plurality of different objects simultaneously at the specimen stage so as to analyze and/or process them one after the other using the respective particle beam apparatus that has the specimen chamber. The specimen stage is embodied to be movable so as to position the object or objects in the specimen chamber. A relative position of the object or objects with respect to an objective lens is set, for example. A known specimen stage is embodied to be movable in three directions which are arranged perpendicular to one another. Moreover, the specimen stage can be rotated about two rotational axes which are arranged perpendicular to one another.

It is known to operate the specimen chamber in different pressure ranges. For example, the specimen chamber is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the specimen chamber is vacuum-sealed during an examination of the object or objects with the particle beam apparatus.

In order to prepare an object for an examination in a particle beam apparatus, the use of a cutting appliance in the form of a microtome is known. Accordingly, the object is prepared by cutting by means of the microtome. Therefore, the microtome is an object preparation device. The microtome has a knife with a cutting bevel. Layers of the object are cut off the object by the knife. Here, the thickness of the layers lies in the range of 0.1 µm to 100 µm, for example. The cut-off layers and/or an area of the object exposed by cutting is/are examined in a particle beam apparatus, for example in an SEM. Typically, biological material is prepared using the microtome. Since, as a rule, biological material has a soft embodiment, the biological material to be examined is embedded in a liquid artificial resin. The artificial resin is cured and consequently rendered cuttable. The biological material embedded in the artificial resin is introduced into the microtome. Then, layers of the biological material are ablated using the microtome and examined in the particle beam apparatus. As an alternative thereto, the exposed areas of the biological material are examined.

The practice of performing the preparation of objects by means of a microtome not only prior to introducing the objects into the specimen chamber of the particle beam apparatus but also in the specimen chamber of a particle beam apparatus itself is known. To this end, the arrangement of a microtome in the specimen chamber of a particle beam apparatus in the form of an SEM is known. A microtome that is arranged in the specimen chamber of a particle beam apparatus is also referred to as an "in situ microtome". Using this known microtome, a layer of the object to be examined is cut, in the specimen chamber that is under vacuum, in such a way that an area to be examined is exposed. This exposed area is then examined using the particle beam of the SEM and imaged by generating an image of the exposed area. The aforementioned steps—specifically exposing an area by cutting material off the object and imaging the exposed area—can be repeated multiple times in succession in order to expose areas anew, which are then examined and imaged using the particle beam of the SEM. In this way, one image is generated in each case of each exposed area. The generated images can be used to create a 3D reconstruction of the object to be examined.

In order to obtain good imaging, the practice of aligning the areas exposed by the microtome perpendicular to the beam axis of the SEM when imaging the areas using the particle beam of the SEM is known. Moreover, the exposed areas should be positionable in the SEM in such a way that an acceptable working distance can be obtained between the objective lens of the SEM and the exposed areas. By way of example, the working distance should lie in the range of 1 mm to 5 mm. In order to obtain a perpendicular alignment of the exposed areas in relation to the beam axis of the SEM and in order to obtain a good working distance of the exposed areas from the objective lens, the practice of arranging the microtome on the adjustable specimen stage of the SEM in the specimen chamber is known. As an alternative thereto, the arrangement of a further adjustable stage for the microtome in the specimen chamber in addition to the specimen stage, the microtome being attached to said further adjustable stage, is known.

The prior art has disclosed a microtome that has a base plate and a stand arranged at the base plate. The stand is embodied as an object receptacle, at which an object to be examined is arranged. Moreover, the stand is embodied to be movable from a first position in the form of an imaging position to a second position in a form of a cutting position by way of a rotation about an axis. The axis is arranged perpendicular to the optical axis of a particle beam apparatus. The known microtome has a knife that can be used to remove layers of the object and that is arranged at the cutting position of the stand. In the known microtome, the stand and consequently also the object are rotated in the direction of the cutting position by way of a rotation of the stand in a first direction (counterclockwise, for example). In the cutting position of the stand, the object strikes the knife such that a layer of the object is cut off by the knife and an area of the object is exposed. Thereupon, the stand is rotated further in the first direction in order to remove cut material that remains on the knife by way of rubbing the knife against a cleaning material. Subsequently, the stand and consequently also the object are rotated into the imaging position in a second direction (clockwise, for example). In the imaging position, the object with the exposed area is moved in the direction of the objective lens in order to set a desired working distance. As an alternative thereto, the objective lens is refocused on the exposed area. Following this, the exposed area of the object is imaged by means of the particle beam of the SEM. The known microtome has a large mass and long adjustment travels of the stand, and so setting a position of the microtome with the specimen stage or the stand is only possible with a great force. Accordingly, motors that have a high power and consequently produce heat are used to set the position of the microtome. The heat is guided, at least in part, into structural units of the microtome. On account of the heating of the structural units, the latter expand. As a result of this, there are inaccuracies when positioning the object, and so the functionality of the microtome, in particular the precise removal of layers of the object, is not always ensured. However, this is not desired. Moreover, in the known microtome, there is a movement of the object under the knife within the scope of the movement of the stand from the cutting position into the imaging position after cutting off a layer of the object using the knife. What may happen during this movement is that contaminants that have remained stuck to the knife despite the cleaning process fall onto the exposed area and, as a result thereof, falsify an imaging of the exposed area. Further, on account of the swivelable stand, the known microtome has a great installation height, and so a positioning of the known microtome with the adjustment travels of the specimen stage of the SEM is not always possible to a sufficient extent.

Further, the prior art has disclosed a microtome in which a knife is guided to the object in order to remove a layer of the object.

In respect of the prior art, reference is made in an exemplary manner to WO 2015/175525 A1 and WO 2008/066846 A2.

SUMMARY OF THE INVENTION

The system described herein is based on the object of specifying an object preparation device and a particle beam apparatus having an object preparation device, in which a contamination of an area that is exposed by a knife is avoided and which facilitate a sufficient positioning of the microtome and of the object while maintaining a good functionality of the microtome.

The object preparation device according to the system described herein is provided for preparing an object in a particle beam apparatus. In some embodiments, the object preparation device has at least one cutting device that is provided with a cutting bevel. Expressed differently, the cutting bevel is arranged at the cutting device. The cutting bevel may be a sharpening on the cutting device which provides the cutting device with its cutting ability. Accordingly, the cutting bevel serves to cut the object. Using the cutting bevel of the cutting device, it is possible to cut layers of the object from the object. By way of example, the thickness of the cut-off layers may lie in the range from 5 nm to 100 μm, including the range boundaries. By way of example, the thickness of the cut-off layers may be 10 nm. However, the system described herein is not restricted to the aforementioned range. Instead, the cutting device of the object preparation device according to the system described herein can be used to cut off layers with any thickness that are suitable for the system described herein.

The object preparation device according to the system described herein further may have a movably embodied object receptacle device having an object receptacle. The object receptacle serves to receive the object. Moreover, the object preparation device according to the system described herein may have at least one drive unit for moving the object receptacle device from a first position of the object receptacle device into a second position of the object receptacle device. The first position of the object receptacle device is an initial position. The object receptacle device may be arranged at the first position in the form of the initial position before the cutting device cuts a layer off the object during the movement of the object receptacle device from the first position to the second position. This is discussed below.

The second position of the object receptacle device may be an analysis and/or processing position of the object receptacle device. An object that is arranged in the object receptacle is able to be analyzed and/or processed in the analysis and/or processing position using the particle beam of the particle beam apparatus. By way of example, the object can be imaged. The object receptacle device may be configured in such a way that it is movable by means of the drive unit, firstly, from the first position into the second position and, secondly, from the second position into the first position.

Moreover, the object preparation device according to the system described herein may have an observation axis that extends through the object receptacle when the object receptacle device is arranged at the second position—i.e., in the analysis and/or processing position. The observation axis may be aligned parallel to a receptacle axis at least touching the object receptacle when the object receptacle device is arranged at the first position. By way of example, the receptacle axis touches the object receptacle at one point. Alternatively, provision is made for e.g. the receptacle axis to partly or completely extend through the object receptacle apparatus and/or the object receptacle. The observation axis may be arranged on a first side of the cutting bevel, wherein the first side may be arranged in a first direction. The receptacle axis may be arranged on a second side of the cutting bevel, wherein the second side may be arranged in a second direction and wherein the first direction and the second direction are diametric. Expressed differently, the first side and the second side are arranged opposite one another such that the observation axis and the receptacle axis are also arranged opposite one another when the object receptacle device is arranged in the first position. Then, the cutting bevel may be arranged between the observation axis and the receptacle axis.

The cutting bevel and the observation axis are arranged spaced apart from one another. Expressed differently, the object preparation device has a first distance between the cutting bevel and the observation axis perpendicular to the observation axis. Moreover, the cutting bevel may be directed in the direction of the object receptacle of the object receptacle device when the object receptacle device is arranged at the first position—i.e., in the initial position. Expressed differently, the cutting bevel of the cutting device points in the direction of the object receptacle of the object receptacle device when the object receptacle device is arranged at the first position.

When the object receptacle device is arranged at the first position, the object receptacle device may be arranged spaced apart from the observation axis. Expressed differently, the object preparation device has a second distance between the object receptacle device arranged at the first position and the observation axis, wherein the second distance may be a distance between the observation axis and the receptacle axis perpendicular to the observation axis.

In the object preparation device according to the system described herein, the first distance may be smaller than the second distance. Expressed differently, the cutting bevel lies closer to the observation axis than the object receptacle of the object receptacle device lies from the observation axis when the object receptacle device is arranged at the first position.

The object preparation device according to the system described herein is advantageous in that the cutting of the object by means of the cutting device takes place during the movement of the object receptacle device from the first position in the form of the initial position into the second position in the form of the analysis and/or processing position of the object receptacle device. Accordingly, after a layer is cut from the object using the cutting device, the object is no longer moved under the cutting device, and so the risk of a contamination of the area exposed by the cutting device by way of dropping material pieces that stayed stuck to the cutting device during the cutting process is avoided. Further, the movably embodied object receptacle device facilitates the use of a drive unit whose heat output is low in comparison with the prior art. This reduces heating of the components of the object preparation device according to the system described herein, and so sufficient positioning of the object receptacle device in a specimen chamber of a particle beam apparatus is possible. The functionality of the object preparation device, in particular the precise removal of layers of the object, is ensured.

The object preparation device according to the system described herein is further advantageous in that forces that occur when removing a layer of the object can only be absorbed by a few small and light components of the object preparation device according to the system described herein. This is different to the prior art, in which very much larger components of the object preparation devices known from the prior art in the form of microtomes have to absorb forces. Consequently, in the object preparation device according to the system described herein, it is possible to embody components of the object preparation device according to the system described herein that need not absorb any forces to be lighter than the components in the prior art. This leads to a lower weight of the object preparation device according to the system described herein in comparison with the known object preparation devices in the form of microtomes in the prior art.

In an embodiment of the object preparation device according to the system described herein, provision is made, additionally or alternatively, for the object receptacle device to be embodied to be movable in a linear fashion. By way of example, provision is made for the object receptacle device to be embodied to be movable in a linear fashion only. In a further embodiment of the object preparation device according to the system described herein, provision is alternatively made for the object preparation device to be movable, at least in part, along a circular path.

In an embodiment of the object preparation device according to the system described herein, provision is made, additionally or alternatively, for the object receptacle to have a receptacle area for the object. Expressed differently, the object is arranged at the receptacle area of the object receptacle. Further, provision is made in the case of the object preparation device for the receptacle axis that extends through the object receptacle to be arranged perpendicular to the receptacle area of the object receptacle. Expressed differently, the receptacle axis that extends through the object receptacle is aligned perpendicular to the receptacle area of the object receptacle. Additionally, or as an alternative thereto, provision is made for the observation axis to be arranged (i.e. aligned) perpendicular to the receptacle area of the object receptacle.

In a further embodiment of the object preparation device according to the system described herein, provision is made, additionally or alternatively, for the object preparation device to be mountable on a movably embodied specimen stage of the particle beam apparatus. Consequently, the object preparation device according to the system described herein can be arranged at the specimen stage that is already arranged in a specimen chamber of the particle beam apparatus. By way of example, the specimen stage is embodied to be movable along a first stage axis, a second stage axis and/or a third stage axis, wherein the first stage axis, the second stage axis and the third stage axis are aligned perpendicular to one another. In a further embodiment, provision is made, additionally or alternatively, for the specimen stage to be embodied to be rotatable about a first stage rotation axis and/or about a second stage rotation axis, wherein the first stage rotation axis is aligned perpendicular to the second stage rotation axis. In a further embodiment, in turn, provision is alternatively made for the object preparation device according to the system described herein to be able to be arranged at a movement stage that is arranged in the specimen chamber of the particle beam apparatus in addition to the specimen stage. Consequently, the specimen chamber of the particle beam apparatus has both the specimen stage and the movement stage.

In an embodiment of the object preparation device according to the system described herein, provision is made, additionally or alternatively, for the object receptacle device to be embodied to be movable in a linear fashion along a first axis. Moreover, the object preparation device has at least one base unit, on which the object receptacle device is arranged, wherein the base unit is embodied to be rotatable about a second axis and wherein the second axis is aligned perpendicular to the first axis. Expressed differently, the object receptacle device moves linearly along the first axis at the base unit. The base unit serves to set the height of the object receptacle device and consequently to set a distance between the area that is arranged at the object receptacle and exposed after a cutting process and an objective lens of the particle beam apparatus.

Consequently, it is possible to always position the exposed area in such a way that the working distance of the exposed area from the objective lens is constant. Therefore, renewed focusing of the objective lens onto an exposed area after a cutting process is not mandatory. Accordingly, focusing the objective lens onto one of the exposed areas of the object a single time is sufficient within the scope of the system described herein. Additionally, or as an alternative thereto, the base unit serves to set the height of the object receptacle device in such a way that the distance of an object from the cutting bevel is always constant. As a result of this, it is possible to ablate successive layers with an identical layer thickness using the cutting bevel without modifying the height position of the cutting bevel. Expressed differently, the height position of the cutting bevel is constant. By way of example, the height corresponds to a perpendicular distance between a reference plane and the cutting bevel along the observation axis, e.g. an optical axis of the particle beam apparatus.

In an embodiment of the object preparation device according to the system described herein, provision is made, additionally or alternatively, for the base unit to be guidable in a movable fashion along the third axis, wherein the third axis is aligned perpendicular to both the first axis and the second axis. By way of example, the third axis is aligned parallel to the observation axis or said third axis corresponds to the observation axis. In particular, provision is made for the first axis to be embodied as x-axis, the second axis to be embodied as y-axis and the third axis to be embodied as z-axis. Consequently, a movement of the base unit along the third axis corresponds to the movement along the z-axis.

In a further embodiment of the object preparation device according to the system described herein, provision is made, additionally or alternatively, for the base unit to have a rhomboid-shaped embodiment. Expressed differently, the base unit has the form of a rhomboid in a side view. Expressed differently in turn, a cut surface of the base unit has the form of a rhomboid. The rhomboid is a quadrilateral in which opposite sides are parallel. The rhomboid is also called parallelogram. In the embodiment described here, the base unit has a first side, a second side, a third side and a fourth side. The first side and the second side are arranged opposite and parallel to one another. The third side and the fourth side are arranged opposite and parallel to one another. Further, the first side and the second side in each case have a longer embodiment than the third side and the fourth side.

In an even further embodiment of the object preparation device according to the system described herein, provision is made, additionally or alternatively, for the base unit to have at least one of the following features:
(i) the first side is connected in articulated fashion to the third side and the fourth side. Expressed differently, the first side is connected to the third side via a first joint and to the fourth side via a second joint;
(ii) the second side is connected in articulated fashion to the third side and the fourth side. Expressed differently, the second side is connected to the third side via a third joint and to the fourth side via a fourth joint;
(iii) the first side is connected in integral fashion to the third side at a first border region between the first side and the third side. The first border region between the first side and the third side is the region at which the first side and the third side contact, for example. By way of example, the first border region is embodied as a first flexure bearing. The first flexure bearing permits relative movement between the first side and the third side by bending;
(iv) the first side is connected in integral fashion to the fourth side at a second border region between the first side and the fourth side. The second border region between the first side and the fourth side is the region at which the first side and the fourth side contact, for example. By way of example, the second border region is embodied as a second flexure bearing. The second flexure bearing permits relative movement between the first side and the fourth side by bending;
(v) the second side is connected in integral fashion to the third side at a third border region between the second side and the third side. The third border region between the second side and the third side is the region at which the second side and the third side contact, for example. By way of example, the third border region is embodied as a third flexure bearing. The third flexure bearing permits relative movement between the second side and the third side by bending;
(vi) the second side is connected in integral fashion to the fourth side at a fourth border region between the second side and the fourth side. The fourth border region between the second side and the fourth side is the region at which the second side and the fourth side contact, for example. By way of example, the fourth border region is embodied as a fourth flexure bearing. The fourth flexure bearing permits relative movement between the second side and the fourth side by bending.

The aforementioned base unit facilitates a relatively low installation height of the object preparation device according to the system described herein while, at the same time, providing a sufficiently large adjustment travel for good positioning of the object receptacle device arranged at the base unit relative to an objective lens of the particle beam apparatus and/or relative to the cutting bevel. By way of example, the installation height of the object preparation device according to the system described herein lies in the range of 30 mm to 45 mm, for example 40 mm. As a result thereof, it is possible to readily assemble the object preparation device according to the system described herein on a specimen stage already present in a particle beam apparatus. Further, as a result of the low installation height, the adjustment travel of the specimen stage along an optical axis of the particle beam apparatus is sufficiently good to set an acceptable working distance between an exposed area and the objective lens. By way of example, the working distance lies in the range of 1 mm to 5 mm. However, the system described herein is not restricted to the aforementioned range. Instead, any working distance that is suitable for the system described herein can be employed. Further, it is possible to readily set the distance of the object from the cutting bevel, as was already explained further above. Moreover, the low installation height ensures a sufficient distance between the object and the objective lens of a particle beam apparatus, and so a detector can be arranged between the object and the objective lens.

In yet another embodiment of the object preparation device according to the system described herein, provision is made, additionally or alternatively, for the object receptacle device to be arranged at the first side of the base unit. The object receptacle device is embodied to be movable at the first side.

In an embodiment of the object preparation device according to the system described herein, provision is made, additionally or alternatively, for a holder to be embodied at the base unit. A first linear actuator is arranged, in turn, at the holder. Further, a spring element is arranged between the object receptacle device and the first linear actuator, wherein the spring element connects the object receptacle device and the first linear actuator. In particular, provision is made for the spring element to have a first end and a second end. The first end of the spring element is arranged at the object receptacle device. The second end of the spring element is arranged at the first linear actuator. The function and mode of operation of the first linear actuator will be discussed further below.

In a further embodiment of the object preparation device according to the system described herein, provision is made, additionally or alternatively, for a second linear actuator for rotating the base unit about the second axis to be arranged at the base unit. By way of example, if the aforementioned base unit with the first side, the second side, the third side and the fourth side is used in the object preparation device according to the system described herein, then the third side or the fourth side, for example, is rotated about the second axis such that the first side is displaced relative to the second side and parallel to the second side along an axis, for example along the observation axis. Further functions and modes of operation of the second linear actuator will be discussed further below.

In yet a further embodiment of the object preparation device according to the system described herein, provision is made, additionally or alternatively, for the object preparation device to have a support wall. At least one third linear actuator is arranged at the object receptacle device, said at least one third linear actuator bracing itself against the support wall for the purposes of moving the object receptacle device. The function and mode of operation of the third linear actuator will be discussed further below. Additionally, or as an alternative thereto, provision is made for the third linear actuator to be arranged at a wall of the object preparation device and for the object receptacle device to have at least one support device. For the purposes of moving the object receptacle device, the third linear actuator braces itself at the support device.

In an even further embodiment of the object preparation device according to the system described herein, provision is made, additionally or alternatively, for a stop device to be arranged at the base unit in order to stop a movement of the object receptacle device from the first position to the second position.

The third linear actuator serves for the linear movement of the object receptacle device, for example along the first side of the base unit. Expressed differently, the third linear actuator produces a force with which a movement of the object receptacle device from the first position in the form of the initial position in the direction of the second position in the form of the analysis and/or processing position is produced. To this end, the third linear actuator braces itself against the support wall, for example. During the movement of the object receptacle device from the first position in the direction of the second position, the object is cut by means of the cutting device—as already explained above. As soon as the cutting process is completed (as soon as a layer of the object has been removed by the cutting device), the third linear actuator is stopped, for example. Then, the further movement of the object receptacle device in the direction of the second position in the form of the analysis and/or processing position is effectuated in this embodiment by means of the first linear actuator, which produces a force in such a way that the object receptacle device is quickly pulled in the direction of the second position and arranged at the second position. By way of example, the stop device can also be used in this context. By way of example, the stop device is arranged in such a way that the object receptacle device is situated in the second position when the stop device is touched by the object receptacle device. Consequently, provision is made, for example, for the movement of the object receptacle device to be stopped as soon as the object receptacle device touches the stop device. Then, the object receptacle device is arranged at the second position. There can be a further movement of the first linear actuator without the object receptacle device being moved further on account of the spring element. Consequently, there is no movement of the object receptacle device beyond the second position. In a further embodiment, the stop device serves to stop the movement of the object receptacle device and to set the position of the object receptacle device at the location of the stop device without the object receptacle device already being situated in the second position. In this embodiment, the object receptacle device is moved into the second position, for example by a movement of the base unit or of the specimen stage on which the object preparation device according to the system described herein is arranged, as soon as the object receptacle device rests against the stop device. In a further embodiment, provision is made for the stop device to be arranged at the second side of the base unit and project through an opening in the first side of the base unit. In this further embodiment, the position of the stop device is fixedly predetermined in respect of the further components of the object preparation device and it does not move, for example when the third side and/or the fourth side of the base unit are rotated about the second axis.

On account of the movement of the second linear actuator, there is a rotation of the base unit about the second axis, for example. As a result of this, the distance between the area that is arranged at the object receptacle and exposed after a cutting process and an objective lens of the particle beam apparatus is set. Consequently, it is possible to always position the exposed area in such a way that the working distance of the exposed area from the objective lens is constant. Therefore, renewed focusing of the objective lens onto an exposed area after a cutting process is not mandatory. Expressed differently, the base unit is guided in a movable fashion along the third axis by way of the rotation of the base unit about the second axis. By way of example, the third axis is aligned parallel to the observation axis or said third axis corresponds to the observation axis. By way of example, if the aforementioned base unit with the first side, the second side, the third side and the fourth side is used in the object preparation device according to the system described herein, then the third side or the fourth side, for example, is rotated about the second axis such that the first side is displaced relative to the second side and parallel to the second side along an axis, for example along the observation axis.

In an embodiment of the object preparation device according to the system described herein, provision is made, additionally or alternatively, for the object preparation device to have at least one pressure sensor for ascertaining a force exerted on the object by the cutting bevel. The pressure ascertained by the pressure sensor can be converted into an exerted force. By way of example, the pressure sensor cooperates with the third linear actuator. In particular, provision is made for the pressure sensor to be arranged at the support wall and/or the support device. By way of example, the pressure sensor serves to obtain data for future applications of the object preparation device according to the system described herein. When moving the object receptacle device with the object in the direction of the cutting bevel, the object strikes the cutting bevel. As a result of this, a force is exerted on the object by means of the cutting bevel. Now, it may be the case that the cutting process is not acceptable in the case of a force that is too high or a force that is too low. By way of example, the cutting process may be incomplete or the object may be damaged. In both cases, the quality of the exposed area is possibly only suitable to a restricted extent for imaging and/or for further analysis by means of a particle beam. By determining the force by means of measuring the pressure using the pressure sensor and by determining the quality of the imaging of the exposed areas that was obtained, it is possible to ascertain a force that is sufficient for the cutting process in such a way that the exposed areas are well suited to imaging and/or a further analysis using a particle beam. This ascertained force is then also used in future for ablating material of the object. In yet a further embodiment of the object preparation device according to the system described herein, the pressure sensor further has the function of determining the distance of the object from the knife. By way of example, there may be a so-called dummy cut at the start of each examination of an object, during which the object is moved toward the cutting bevel but no layer of the object is removed by the cutting bevel as the latter does not touch the object during the movement of the object in the direction of the second position. This is determinable by means of the pressure sensor since the force determined by means of the pressure sensor does not change in that case. In this case, the object is moved in the direction of the cutting bevel by means of the base unit and/or the specimen stage, for example. Then, there is, once again, a movement of the object receptacle device together with the object in the direction of the second position, for example. If the cutting bevel now strikes the object, this is indicated by an increased pressure at the pressure sensor. In an even further embodiment, the pressure sensor is used to ascertain properties of the object. By way of example, if the object is provided with hard inclusions that render a removal of a layer impossible, these inclusions are ascertained, by means of the pressure sensor, by way of a force to be applied to the object being exceeded. The same applies if the cutting bevel only strikes the object receptacle device but not the object itself, for example. This can likewise be ascertained by a certain force being exceeded by way of a measurement by means of the pressure sensor.

In an embodiment of the object preparation device according to the system described herein, provision is made, additionally or alternatively, for the object preparation device to have at least one base plate, at least one first sidewall and at least one second sidewall. The base plate is arranged at the first sidewall at a first angle that differs from 0° and 180°. By way of example, the first angle is 90° or substantially 90°. Further, the second sidewall is arranged at the first sidewall at a second angle that differs from 0° and 180°. By way of example, the second angle is 90° or substantially 90°. The base plate and the second sidewall are spaced apart from one another. Further, the base plate, the first sidewall and the second sidewall include a space in which the object receptacle device is arranged when the object receptacle device is arranged at the first position.

In a further embodiment of the object preparation device according to the system described herein, provision is made, additionally or alternatively, for the object preparation device to have at least one sensor for determining the position of the object and/or the distance of the object from the cutting bevel. By way of example, the position of the object and/or the distance of the object from the cutting bevel is determined by way of an indirect determination, in which the distance of the sensor from a detection area of the object receptacle device is initially ascertained and the position of the object and/or the distance of the object from the cutting bevel is subsequently determined on the basis of the predetermined geometric conditions. As a result of this, it is possible, in particular, to monitor the movement of the object receptacle device along the third axis and/or to set the position of the object receptacle device along the third axis. Moreover, provision is made additionally or alternatively for the object preparation device to have at least one cutting device drive for moving the cutting bevel. By way of example, the object preparation device has a piezo motor which moves the cutting device and consequently the cutting bevel in an oscillating fashion. Consequently, an oscillating cutting movement is provided, which is particularly expedient for removing a layer of the object. Further, it is possible to set both the cutting speed of the cutting device by setting a cutting frequency and the amplitude of the cutting movement of the cutting device. As a result of this, it is possible to obtain particularly good cutting conditions. By way of example, the pressure sensor is used to set and/or optimize the cutting speed and/or the cutting frequency.

The system described herein also relates to a further object preparation device for preparing an object in a particle beam apparatus, having at least one pressure sensor for ascertaining a force that is exerted by a cutting bevel on an object. By way of example, this further object preparation device has at least one of the features specified further above or yet to be specified below or a combination of at least two of the features specified further above or yet to be specified below. In particular, provision is made in this further object preparation device for the pressure ascertained by the pressure sensor to be converted into an exerted force. By way of example, the pressure sensor cooperates with a third linear actuator, which was described further above. In particular, provision is made for the pressure sensor to be arranged at the support wall of the object preparation device and/or a support device of an object receptacle device. By way of example, the pressure sensor serves to obtain data for future applications of the object preparation device according to the system described herein. By way of example, the pressure sensor of this further object preparation device has the functions and effects that were specified above or are yet to be specified below. These are referred to explicitly here.

The system described herein also relates to an even further object preparation device for preparing an object in a particle beam apparatus, having at least one base unit on which an object receptacle device with an object receptacle for receiving an object is arranged. The base unit of this even further object preparation device is embodied in a movable fashion and has at least one flexure bearing. In particular, provision is made for this even further object preparation device to have at least one of the features specified further above or yet to be specified below or a combination of at least two of the features specified further above or yet to be specified below. In particular, the base unit has at least one of the features specified further above or yet to be specified below or a combination of at least two of the features specified further above or yet to be specified below. By means of the base unit of this even further object preparation device, it is possible to position an object along an axis. By way of example, this is the optical axis of a particle beam apparatus or an axis that is aligned parallel to the optical axis of a particle beam apparatus.

The system described herein also relates to yet a further object preparation device for preparing an object in a particle beam apparatus, having at least one object receptacle device with an object receptacle for receiving an object. The further object preparation device has a first drive and a second drive for a linear movement of the object receptacle device along an axis. The first drive has a uniform driving force and provides a slow movement, for example. This first drive is used to move the object receptacle device with the object in the direction of the cutting bevel. In comparison with the first drive, the second drive is a fast drive which, however, is not as positionally accurate as the first drive. The second drive can cooperate with a stop device. The first drive has a high power and accordingly emits heat. However, the second drive produces less heat than the first drive. As a result of this, less heat is guided into the components of the further object preparation device, and so the components expand to a lesser extent in comparison with the prior art. By way of example, the first drive is embodied as the aforementioned third linear actuator. The second drive is embodied as the aforementioned first linear actuator, for example. In addition, or as an alternative thereto, provision is made for this further object preparation device to have at least one of the features specified further above or yet to be specified below or a combination of at least two of the features specified further above or yet to be specified below. It has emerged that this further object preparation device renders it possible to use smaller and lighter components in the further object preparation device according to the system described herein when compared to the prior art. This leads to the lower weight of the further object preparation device according to the system described herein, already mentioned above, in comparison with the known object preparation devices in the prior art.

The system described herein also relates to a particle beam apparatus. By way of example, the particle beam apparatus according to the system described herein is embodied as an electron beam apparatus and/or as an ion beam apparatus. The particle beam apparatus according to the system described herein serves for analyzing, in particular for imaging, and/or for processing an object. The particle beam apparatus according to the system described herein has at least one beam generator for generating a particle beam comprising charged primary particles.

By way of example, the primary particles are electrons or ions. The particle beam apparatus according to the system described herein furthermore has at least one objective lens for focusing the particle beam onto the object, wherein interaction particles and/or interaction radiation is/are generated upon interaction between the particle beam and the object. The interaction particles are, for example, secondary particles, in particular secondary electrons, and/or backscattered particles, for example backscattered electrons. By way of example, the interaction radiation is x-ray radiation or cathodoluminescence. Further, the particle beam apparatus according to the system described herein has at least one optical axis, along which the particle beam can be guided. Moreover, the particle beam apparatus according to the system described herein has at least one detector for detecting the interaction particles and/or interaction radiation. The particle beam apparatus according to the system described herein also has at least one object preparation device, wherein the object preparation device has at least one of the features specified above or yet to be specified below or a combination of at least two of the features specified above or yet to be specified below. Further, provision is made for the observation axis of the object preparation device to correspond to the optical axis of the particle beam apparatus.

In an embodiment of the particle beam apparatus according to the system described herein, provision is made, additionally or alternatively, for the particle beam apparatus to have at least one of the following features:

(i) the object preparation device is arranged at a movably embodied specimen stage of the particle beam apparatus, wherein the specimen stage is embodied to be movable along a first stage axis, a second stage axis and/or a third stage axis, wherein the first stage axis, the second stage axis and the third stage axis are aligned perpendicular to one another;

(ii) the object preparation device is arranged at a movably embodied specimen stage of the particle beam apparatus, wherein the specimen stage is embodied to be movable along a first stage axis, a second stage axis and/or a third stage axis, wherein the first stage axis, the second stage axis and the third stage axis are aligned perpendicular to one another, wherein the specimen stage is embodied to be rotatable about a first stage rotation axis and/or about a second stage rotation axis, wherein the first stage rotation axis is aligned perpendicular to the second stage rotation axis.

In a yet further embodiment of the particle beam apparatus according to the system described herein, provision is made, additionally or alternatively, for the particle beam apparatus to have at least one mirror corrector for correcting chromatic and/or spherical aberration.

As already mentioned above, provision is made, additionally or alternatively, in an embodiment of the particle beam apparatus according to the system described herein for the particle beam apparatus to be embodied as an electron beam apparatus and/or as an ion beam apparatus.

In yet a further embodiment of the particle beam apparatus according to the system described herein, provision is made, additionally or alternatively, for the beam generator for generating a particle beam comprising charged primary particles to be embodied as a first beam generator for generating a first particle beam comprising first charged primary particles and for the objective lens to be embodied as a first objective lens for focusing the first particle beam onto the object. Furthermore, the particle beam apparatus has at least one second beam generator for generating a second particle beam comprising second charged primary particles, and at least one second objective lens for focusing the second particle beam onto the object. The second charged primary particles are electrons or ions, for example.

The system described herein also relates to a method for operating the particle beam apparatus, having at least one of the features specified further above or yet to be specified below or with a combination of at least two of the features specified further above or yet to be specified below. In the method according to the system described herein, provision is made for the distance of the object from the cutting bevel to be set, for example by rotating the base unit about the second axis. Further, the object receptacle device is moved from the first position in the direction of the second position, wherein a layer of an object is removed by the cutting bevel during this movement of the object receptacle device such that an area of the object is exposed. Then, the particle beam is guided to this exposed area when the object receptacle device is arranged in the second position. On account of the interaction of the particle beam with the exposed area, the interaction particles and/or the interaction radiation are/is generated. The interaction particles and/or the interaction radiation are detected by the detector. The detector generates detection signals. The exposed area is analyzed by means of the detection signals. In particular, an image of the exposed area is created. The aforementioned method steps can be repeated in one embodiment of the method according to the system described herein in order to expose an area anew, said area then being analyzed, in particular imaged, by means of the particle beam. In this way, one image or a plurality of images is/are generated in each case of each exposed area. The images generated from each exposed area can be used to create a 3D reconstruction of the object to be examined.

The system described herein also relates to a further particle beam apparatus for analyzing and/or processing an object, wherein the further particle beam apparatus has at least one of the features specified further above or yet to be specified below or a combination of at least two of the features specified further above or yet to be specified below, for example. The further particle beam apparatus has a specimen chamber and at least one particle-optical column for generating and guiding a particle beam comprising charged primary particles, wherein the particle-optical column defines an optical axis along which the particle beam is guidable in the particle beam apparatus from a particle beam generator to the specimen chamber. The further particle beam apparatus further has at least one detector for detecting interaction particles and/or interaction radiation of an interaction of the particle beam with the object, and at least one object preparation device having a cutting device, which has a cutting bevel, and having an object receptacle for receiving the object. The object receptacle is embodied to be movable in a plane that is substantially perpendicular or perpendicular to the optical axis of the particle-optical column. The cutting device is aligned in such a way that the cutting bevel thereof extends in a plane that is aligned parallel to the plane substantially perpendicular or perpendicular to the optical axis of the particle-optical column and is arranged at the cutting device at a side distant from the optical axis of the particle-optical column.

The system described herein also relates to a further object preparation device for preparing an object in a particle beam apparatus, wherein the further object preparation device has at least one of the features specified further above or yet to be specified below or a combination of at least two of the features specified further above or yet to be specified below, for example. The further object preparation device has a cutting device, which has a cutting bevel, and an object receptacle for receiving the object, wherein the object receptacle is adjustable along a linear trajectory. Further, the further object preparation device has a first linear actuator and a third linear actuator which are configured to drive the object receptacle along the same linear trajectory. Moreover, the further object preparation device has a controller that is configured to actuate the third linear actuator for taking a section of the object and, after taking the section, to actuate the first linear actuator for positioning the object along the linear trajectory in an observation position of the particle beam apparatus, wherein the movement of the object receptacle for taking the section and the positioning of the object at the observation position are carried out without reversing the direction along the linear trajectory.

BRIEF DESCRIPTION OF THE DRAWINGS

The system described herein will be explained in more detail below on the basis of illustrative embodiments using drawings. In the figures.

DETAILED DESCRIPTION OF VARIOUS EMBODIMENTS

Some embodiments of the system described herein are now explained in more detail by means of particle beam apparatuses in the form of an SEM and in the form of a combination apparatus, which has an electron beam column and an ion beam column. Reference is explicitly made to the fact that the system described herein may be used in any particle beam apparatus, in particular in every electron beam apparatus and/or in every ion beam apparatus.

Figure 1:
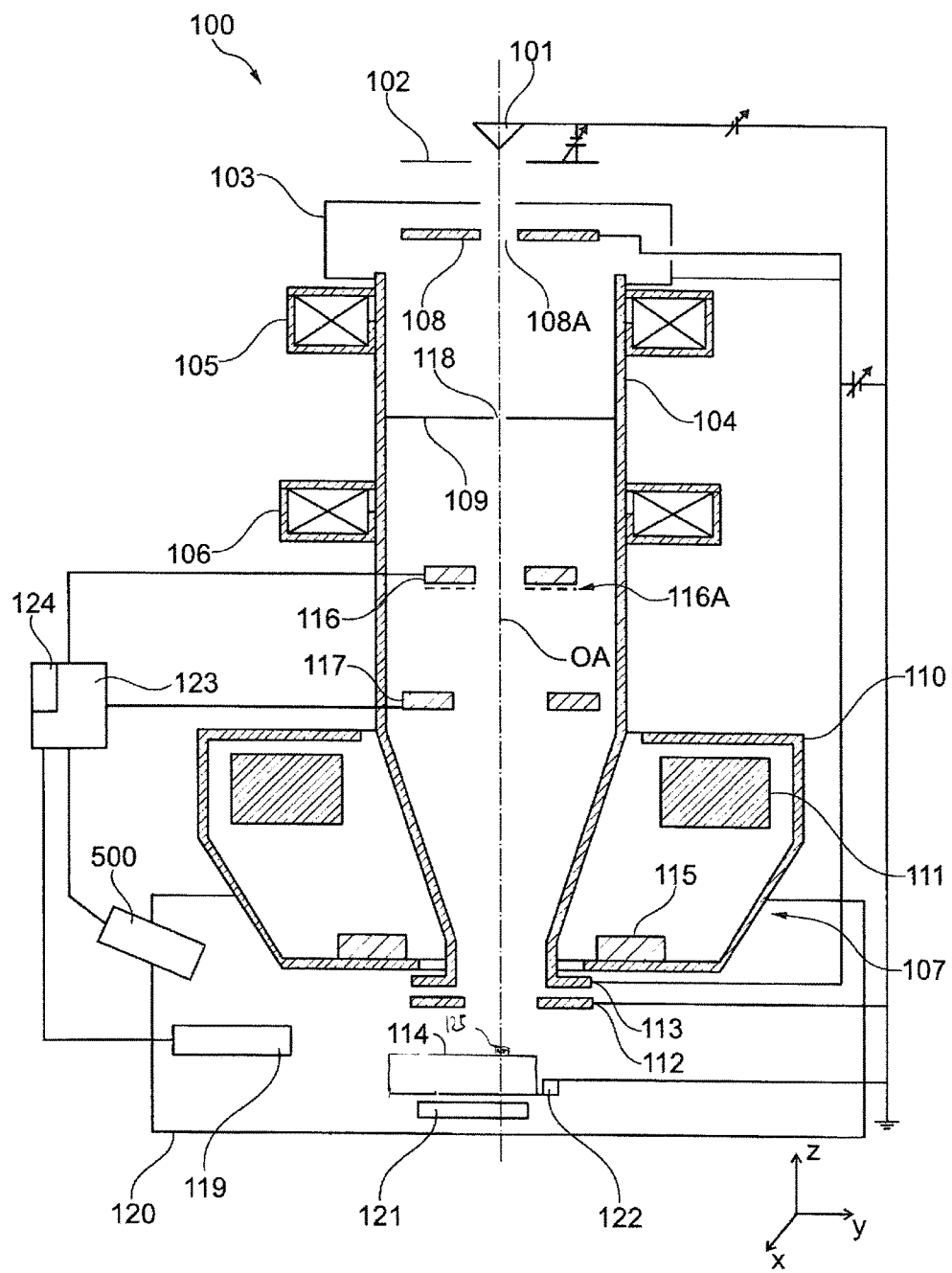
FIG. 1 shows a first illustrative embodiment of a particle beam apparatus, according to an embodiment of the system described herein.

FIG. 1 shows a schematic illustration of an SEM 100, according to an embodiment of the system described herein. The SEM 100 comprises a first beam generator in the form of an electron source 101, which may be embodied as a cathode. Further, the SEM 100 may be provided with an extraction electrode 102 and with an anode 103, which is placed onto one end of a beam-guiding tube 104 of the SEM 100. By way of example, the electron source 101 is embodied as a thermal field emitter. However, the system described herein is not restricted to such an electron source 101. Rather, any electron source is utilizable.

Electrons emerging from the electron source 101 form a primary electron beam. The electrons are accelerated to the anode potential due to a potential difference between the electron source 101 and the anode 103. In the illustrative embodiment depicted here, the anode potential is 1 kV to 20 kV, e.g. 5 kV to 15 kV, in particular 8 kV, in relation to a ground potential of a housing of a specimen chamber 120. However, alternatively it could be at ground potential.

Two condenser lenses, namely a first condenser lens 105 and a second condenser lens 106, are arranged at the beam-guiding tube 104. Here, proceeding from the electron source 101 as viewed in the direction of a first objective lens 107, the first condenser lens 105 is arranged first, followed by the second condenser lens 106. Reference is explicitly made to the fact that further illustrative embodiments of the SEM 100 may have only a single condenser lens. A first aperture unit 108 is arranged between the anode 103 and the first condenser lens 105. Together with the anode 103 and the beam-guiding tube 104, the first aperture unit 108 is at a high voltage potential, namely the potential of the anode 103, or it is connected to ground. The first aperture unit 108 has numerous first apertures 108A, of which one is depicted in FIG. 1. Two first apertures 108A are present, for example. Each one of the numerous first apertures 108A has a different aperture diameter. By means of an adjustment mechanism (not depicted here), it is possible to set a desired first aperture 108A onto an optical axis OA of the SEM 100. Reference is explicitly made to the fact that, in further illustrative embodiments, the first aperture unit 108 may be provided with only a single aperture 108A. In this illustrative embodiment, an adjustment mechanism may be omitted. The first aperture unit 108 is then designed in a stationary fashion. A stationary second aperture unit 109 is arranged between the first condenser lens 105 and the second condenser lens 106. As an alternative thereto, provision is made for the second aperture unit 109 to be embodied in a movable fashion.

In some embodiments, the first objective lens 107 has pole pieces 110, in which a bore is formed. The beam-guiding tube 104 is guided through this bore. A coil 111 is arranged in the pole pieces 110.

In some embodiments, a electrostatic retardation device is arranged in a lower region of the beam-guiding tube 104. It has a single electrode 112 and a tube electrode 113. The tube electrode 113 is arranged at one end of the beam-guiding tube 104, which faces an object 125 that is arranged in an object preparation device in the form of a microtome 114. The microtome 114 is explained in more detail below. Together with the beam-guiding tube 104, the tube electrode 113 is at the potential of the anode 103, while the single electrode 112 and the object 125 are at a lower potential in relation to the potential of the anode 103. In the present case, this is the ground potential of the housing of the specimen chamber 120. In this manner, the electrons of the primary electron beam may be decelerated to a desired energy which is required for examining the object 125.

In some embodiments, the SEM 100 further comprises a scanning device 115, by means of which the primary electron beam may be deflected and scanned over the object 125. Here, the electrons of the primary electron beam interact with the object 125. As a result of the interaction, interaction particles are generated, which are detected. In particular, electrons are emitted from the surface of the object 125—the so-called secondary electrons—or electrons of the primary electron beam are scattered back—the so-called backscattered electrons—as interaction particles.

The object 125 and the single electrode 112 may also be at different potentials and potentials different than ground. It is thereby possible to set the location of the retardation of the primary electron beam in relation to the object 125. By way of example, if the retardation is carried out quite close to the object 125, optical aberrations become smaller.

In some embodiments, a detector arrangement comprising a first detector 116 and a second detector 117 is arranged in the beam-guiding tube 104 for detecting the secondary electrons and/or the backscattered electrons. Here, the first detector 116 is arranged on the source-side along the optical axis OA, while the second detector 117 is arranged on the object-side along the optical axis OA in the beam-guiding tube 104. The first detector 116 and the second detector 117 are arranged offset from one another in the direction of the optical axis OA of the SEM 100. Both the first detector 116 and the second detector 117 each have a passage opening, through which the primary electron beam may pass. The first detector 116 and the second detector 117 are approximately at the potential of the anode 103 and of the beam-guiding tube 104. The optical axis OA of the SEM 100 extends through the respective passage openings.

The second detector 117 serves principally for detecting secondary electrons. Upon emerging from the object 125, the secondary electrons initially have a low kinetic energy and arbitrary directions of motion. By means of the strong extraction field emanating from the tube electrode 113, the secondary electrons are accelerated in the direction of the first objective lens 107. The secondary electrons enter the first objective lens 107 approximately parallel. The beam diameter of the beam of secondary electrons remains small in the first objective lens 107 as well. The first objective lens 107 then has a strong effect on the secondary electrons and generates a comparatively short focus of the secondary electrons with sufficiently steep angles with respect to the optical axis OA, such that the secondary electrons diverge far apart from one another downstream of the focus and are incident on the second detector 117 on the active area thereof. By contrast, only a small proportion of electrons that are backscattered at the object 125—that is to say backscattered electrons which have a relatively high kinetic energy in comparison with the secondary electrons upon emerging from the object 125—are detected by the second detector 117. The high kinetic energy and the angles of the backscattered electrons with respect to the optical axis OA upon emerging from the object 125 have the effect that a beam waist, that is to say a beam region having a minimum diameter, of the backscattered electrons lies in the vicinity of the second detector 117. A large portion of the backscattered electrons passes through the passage opening of the second detector 117. Therefore, the first detector 116 substantially serves to detect the backscattered electrons.

In a further embodiment of the SEM 100, the first detector 116 may additionally be embodied with an opposing field grating 116A. The opposing field grating 116A is arranged at the side of the first detector 116 directed toward the object 125. With respect to the potential of the beam-guiding tube 104, the opposing field grating 116A has a negative potential such that only backscattered electrons with a high energy pass through the opposing field grating 116A to the first detector 116. Additionally or alternatively, the second detector 117 has a further opposing field grating, which has an analogous embodiment to the aforementioned opposing field grating 116A of the first detector 116 and which has an analogous function.

Further, the SEM 100 has in the specimen chamber 120 a chamber detector 119, for example an Everhart-Thornley detector or an ion detector which has a detection surface that is coated with metal and blocks light.

The detection signals generated by the first detector 116, the second detector 117 and the chamber detector 119 are used to generate an image or images of the surface of the object 125.

Reference is explicitly made to the fact that the apertures of the first aperture unit 108 and of the second aperture unit 109, as well as the passage openings of the first detector 116 and of the second detector 117 are depicted in exaggerated fashion. The passage opening of the first detector 116 and of the second detector 117 have an extent perpendicular to the optical axis OA in the range of 0.5 mm to 5 mm. By way of example, they are of circular design and have a diameter in the range of 1 mm to 3 mm perpendicular to the optical axis OA.

The second aperture unit 109 is configured as a pinhole aperture in the illustrative embodiment depicted here and provided with a second aperture 118 for the passage of the primary electron beam, which has an extent in the range from 5 µm to 500 µm, e.g. 35 µm. As an alternative thereto, provision is made in a further embodiment for the second aperture unit 109 to be provided with a plurality of apertures, which can be displaced mechanically with respect to the primary electron beam or which can be reached by the primary electron beam by the use of electrical and/or magnetic deflection elements. The second aperture unit 109 is embodied as a pressure stage stop. It separates a first region, in which the electron source 101 is arranged and in which an ultra-high vacuum ($10^{-7}$ hPa to $10^{-12}$ hPa) prevails, from a second region, which has a high vacuum ($10^{-3}$ hPa to $10^{-7}$ hPa). The second region is the intermediate pressure region of the beam-guiding tube 104, which leads to the specimen chamber 120.

In some embodiments, the specimen chamber 120 is under vacuum. For the purposes of producing the vacuum, a pump (not illustrated) is arranged at the specimen chamber 120. In the illustrative embodiment illustrated in FIG. 1, the specimen chamber 120 is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the specimen chamber 120 is vacuum-sealed.

In some embodiments, the microtome 114 is arranged at a specimen stage 122. The specimen stage 122 is embodied to be movable in three directions arranged perpendicular to one another, namely in an x-direction (first stage axis), in a y-direction (second stage axis) and in a z-direction (third stage axis). Moreover, the specimen stage 122 can be rotated about two rotational axes which are arranged perpendicular to one another (stage rotation axes).

In some embodiments, the SEM 100 further comprises a third detector 121, which is arranged in the specimen chamber 120. More precisely, the third detector 121 is arranged downstream of the microtome 114, as seen from the electron source 101 along the optical axis OA. The microtome 114 can be rotated in such a way that the object 125 that is arranged in the microtome 114 can have the primary electron beam radiated therethrough. When the primary electron beam passes through the object 125 to be examined, the electrons of the primary electron beam interact with the material of the object 125 to be examined. The electrons passing through the object 125 to be examined are detected by the third detector 121.

In some embodiments, arranged at the specimen chamber 120 is a radiation detector 500, which is used to detect interaction radiation, for example x-ray radiation and/or cathodoluminescence. The radiation detector 500, the first detector 116, the second detector 117 and the chamber detector 119 are connected to a monitoring unit 123, which has a monitor 124. The third detector 121 is also connected to the monitoring unit 123. For reasons of clarity, this is not illustrated. The monitoring unit 123 processes detection signals that are generated by the first detector 116, the second detector 117, the chamber detector 119, the third detector 121 and/or the radiation detector 500 and displays on the monitor 124 said detection signals in the form of images.

Figure 2:
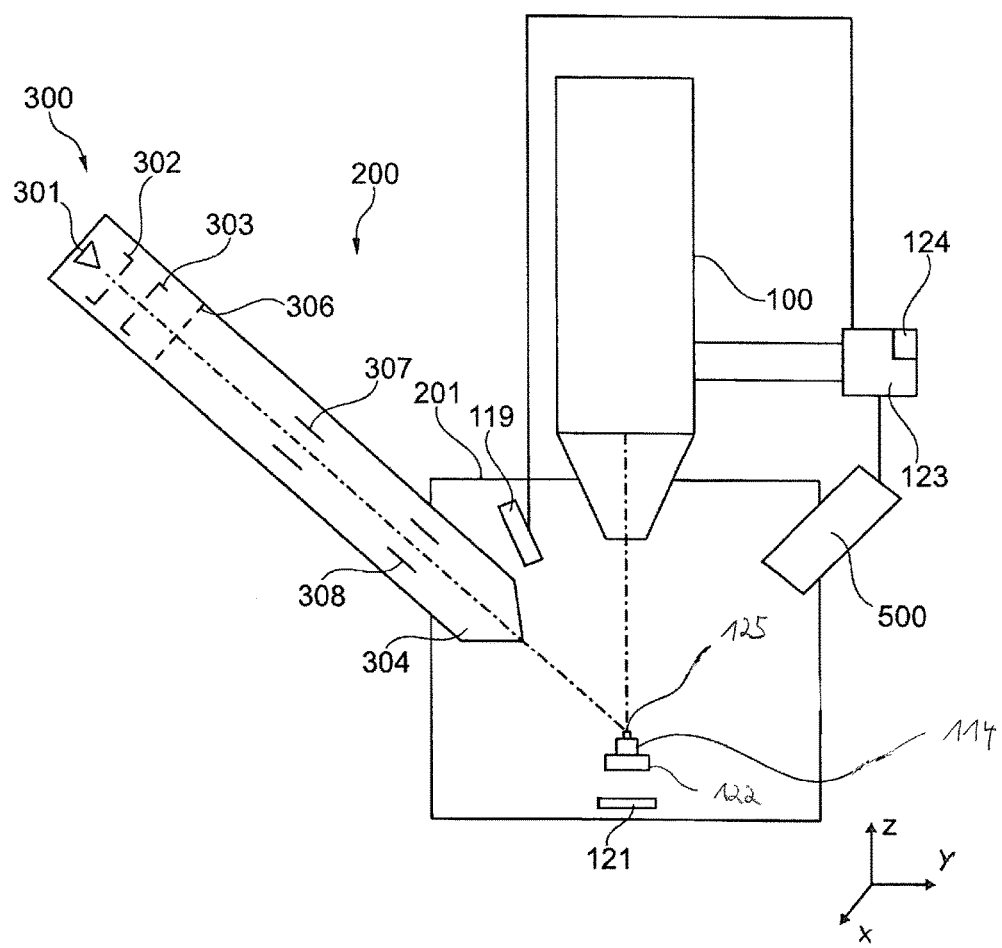
FIG. 2 shows a second illustrative embodiment of a particle beam apparatus, according to an embodiment of the system described herein.

FIG. 2 shows a particle beam apparatus in the form of a combination apparatus 200, according to an embodiment of the system described herein. The combination apparatus 200 has two particle beam columns. On the one hand, the combination apparatus 200 is provided with the SEM 100, as already depicted in FIG. 1, but without the specimen chamber 120. Rather, the SEM 100 is arranged at a specimen chamber 201. The specimen chamber 201 is under vacuum. For the purposes of producing the vacuum, a pump (not illustrated) is arranged at the specimen chamber 201. In the illustrative embodiment illustrated in FIG. 2, the specimen chamber 201 is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the specimen chamber 201 is vacuum-sealed.

In some embodiments, arranged in the specimen chamber 201 is a chamber detector 119 which is embodied, for example, in the form of an Everhart-Thornley detector or an ion detector and which has a detection surface coated with metal that blocks light. Further, the third detector 121 is arranged in the specimen chamber 201.

The SEM 100 serves to generate a first particle beam, namely the primary electron beam already described further above. On the other hand, the combination apparatus 200 is provided with an ion beam apparatus 300, which is likewise arranged at the specimen chamber 201.

The SEM 100 is arranged vertically in relation to the specimen chamber 201. By contrast, the ion beam apparatus 300 is arranged inclined by an angle of approximately 50° in relation to the SEM 100. It has a second beam generator in the form of an ion beam generator 301. Ions, which form a second particle beam in the form of an ion beam, are generated by the ion beam generator 301. The ions are accelerated by means of an extraction electrode 302, which is at a predeterminable potential. The second particle beam then passes through ion optics of the ion beam apparatus 300, wherein the ion optics comprise a condenser lens 303 and a second objective lens 304. The second objective lens 304 ultimately generates an ion probe, which is focused on the object 125 arranged in an object preparation device in the form of a microtome 114. The microtome 114 is arranged at a specimen stage 122.

In some embodiments, an adjustable or selectable aperture device 306, a first electrode arrangement 307 and a second electrode arrangement 308 are arranged above the second objective lens 304 (i.e. in the direction of the ion beam generator 301), wherein the first electrode arrangement 307 and the second electrode arrangement 308 are embodied as scanning electrodes. The second particle beam is scanned over the surface of the object 125 by means of the first electrode arrangement 307 and the second electrode arrangement 308, with the first electrode arrangement 307 acting in a first direction and the second electrode arrangement 308 acting in a second direction, which is counter to the first direction. Using this, scanning is carried out in e.g. an x-direction. The scanning in a y-direction perpendicular thereto is brought about by further electrodes (not depicted here), which are rotated by 90°, at the first electrode arrangement 307 and at the second electrode arrangement 308.

As discussed above, the microtome 114 is arranged at the specimen stage 122. In the illustrative embodiment shown in FIG. 2, the specimen stage 122 is also embodied to be movable in three directions arranged perpendicular to one another, namely in an x-direction (first stage axis), in a y-direction (second stage axis) and in a z-direction (third stage axis). Moreover, the specimen stage 122 can be rotated about two rotational axes which are arranged perpendicular to one another (stage rotation axes).

The distances depicted in FIG. 2 between the individual units of the combination apparatus 200 are depicted in exaggerated fashion in order to better depict the individual units of the combination apparatus 200.

In some embodiments, arranged at the specimen chamber 201 is a radiation detector 500, which is used to detect interaction radiation, for example x-ray radiation and/or cathodoluminescence. The radiation detector 500 is connected to a monitoring unit 123, which has a monitor 124. The monitoring unit 123 processes detection signals that are generated by the first detector 116, the second detector 117 (not illustrated in FIG. 2), the chamber detector 119, the third detector 121 and/or the radiation detector 500 and displays on the monitor 124 said detection signals in the form of images.

Figure 3:
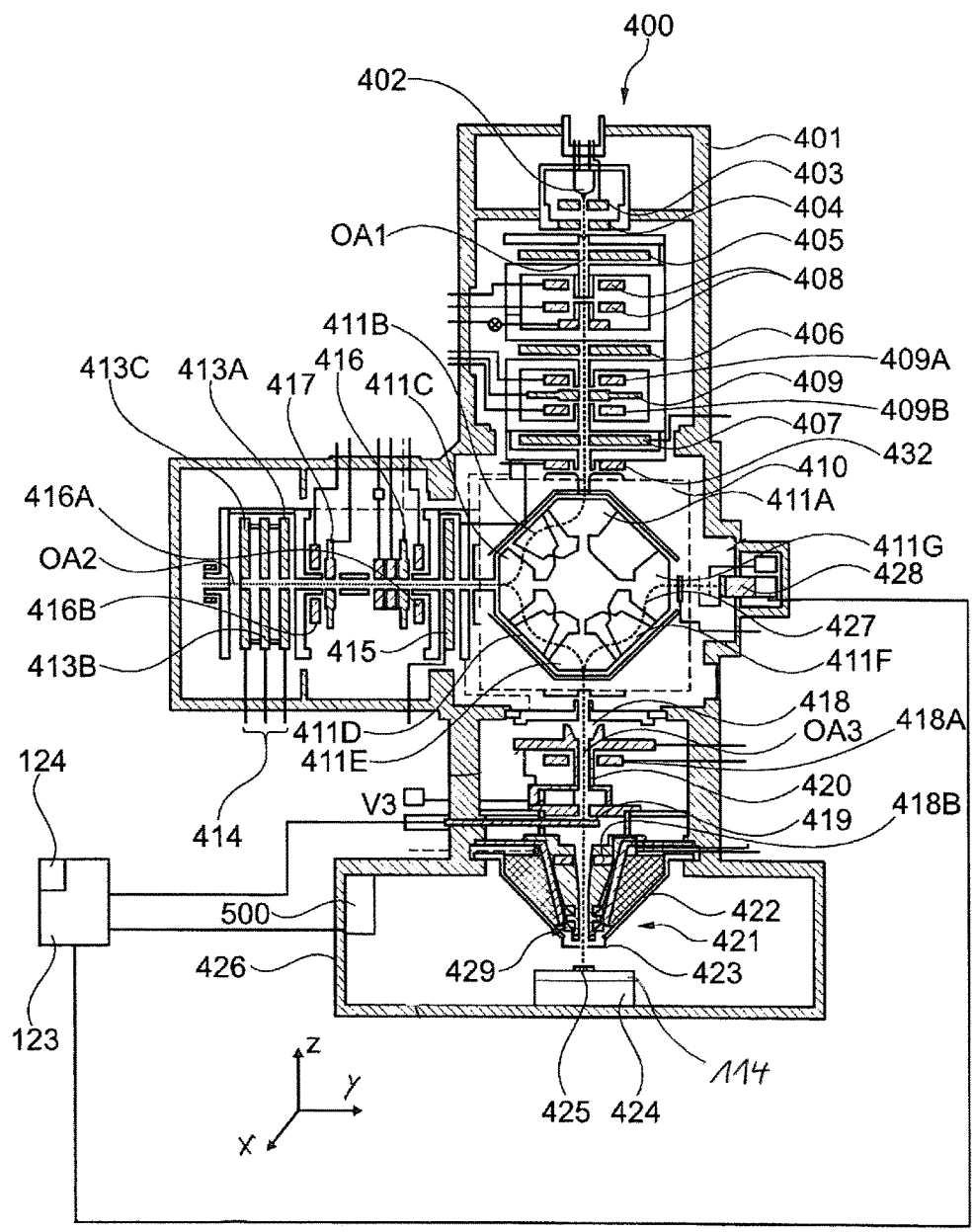
FIG. 3 shows a third illustrative embodiment of a particle beam apparatus, according to an embodiment of the system described herein.

FIG. 3 is a schematic illustration of a further illustrative embodiment of a particle beam apparatus according to the system described herein. This illustrative embodiment of the particle beam apparatus is provided with the reference sign 400 and said illustrative embodiment comprises a mirror corrector for correcting e.g. chromatic and/or spherical aberrations. The particle beam apparatus 400 comprises a particle beam column 401, which is embodied as an electron beam column and which substantially corresponds to an electron beam column of a corrected SEM. However, the particle beam apparatus 400 is not restricted to an SEM with a mirror corrector. Rather, the particle beam apparatus may comprise any type of correction units.

The particle beam column 401 comprises a particle beam generator in the form of an electron source 402 (cathode), an extraction electrode 403, and an anode 404. By way of example, the electron source 402 is embodied as a thermal field emitter. Electrons emerging from the electron source 402 are accelerated to the anode 404 due to a potential difference between the electron source 402 and the anode 404. Accordingly, a particle beam in the form of an electron beam is formed along a first optical axis OA1.

The particle beam is guided along a beam path, which corresponds to the first optical axis OA1, after the particle beam has emerged from the electron source 402. A first electrostatic lens 405, a second electrostatic lens 406, and a third electrostatic lens 407 are used to guide the particle beam.

Furthermore, in some embodiments, the particle beam is adjusted along the beam path using a beam-guiding device. The beam-guiding device of this illustrative embodiment comprises a source adjustment unit with two magnetic deflection units 408 arranged along the first optical axis OA1. Moreover, the particle beam apparatus 400 comprises electrostatic beam deflection units. A first electrostatic beam deflection unit 409, which is also embodied as a quadrupole in a further embodiment, is arranged between the second electrostatic lens 406 and the third electrostatic lens 407. The first electrostatic beam deflection unit 409 is likewise arranged downstream of the magnetic deflection units 408. A first multi-pole unit 409A in the form of a first magnetic deflection unit is arranged at one side of the first electrostatic beam deflection unit 409. Moreover, a second multi-pole unit 409B in the form of a second magnetic deflection unit is arranged at the other side of the first electrostatic beam deflection unit 409. The first electrostatic beam deflection unit 409, the first multi-pole unit 409A, and the second multi-pole unit 409B are set for the purposes of setting the particle beam in respect of the axis of the third electrostatic lens 407 and the entrance window of a beam deflection device 410. The first electrostatic beam deflection unit 409, the first multi-pole unit 409A and the second multi-pole unit 409B may interact like a Wien filter. A further magnetic deflection element 432 is arranged at the entrance to the beam deflection device 410.

The beam deflection device 410 is used as a particle beam deflector, which deflects the particle beam in a specific manner. In some embodiments, the beam deflection device 410 comprises a plurality of magnetic sectors, namely a first magnetic sector 411A, a second magnetic sector 411B, a third magnetic sector 411C, a fourth magnetic sector 411D, a fifth magnetic sector 411E, a sixth magnetic sector 411F, and a seventh magnetic sector 411G. The particle beam enters the beam deflection device 410 along the first optical axis OA1 and said particle beam is deflected by the beam deflection device 410 in the direction of a second optical axis OA2. The beam deflection is performed by means of the first magnetic sector 411A, by means of the second magnetic sector 411B and by means of the third magnetic sector 411C through an angle of 30° to 120°. The second optical axis OA2 is oriented at the same angle with respect to the first optical axis OA1. The beam deflection device 410 also deflects the particle beam which is guided along the second optical axis OA2, to be precise in the direction of a third optical axis OA3. The beam deflection is provided by the third magnetic sector 411C, the fourth magnetic sector 411D, and the fifth magnetic sector 411E. In the illustrative embodiment in FIG. 3, the deflection with respect to the second optical axis OA2 and with respect to the third optical axis OA3 is provided by deflecting the particle beam at an angle of 90°. Hence, the third optical axis OA3 extends coaxially with respect to the first optical axis OA1. However, reference is made to the fact that the particle beam apparatus 400 according to the system described herein is not restricted to deflection angles of 90°. Rather, any suitable deflection angle may be selected by the beam deflection device 410, for example 70° or 110°, such that the first optical axis OA1 does not extend coaxially with respect to the third optical axis OA3. In respect of further details of the beam deflection device 410, reference is made to WO 2002/067286 A2.

After the particle beam was deflected by the first magnetic sector 411A, the second magnetic sector 411B, and the third magnetic sector 411C, the particle beam is guided along the second optical axis OA2. The particle beam is guided to an electrostatic mirror 414 and travels on its path to the electrostatic mirror 414 along a fourth electrostatic lens 415, a third multi-pole unit 416A in the form of a magnetic deflection unit, a second electrostatic beam deflection unit 416, a third electrostatic beam deflection unit 417, and a fourth multi-pole unit 416B in the form of a magnetic deflection unit. The electrostatic mirror 414 comprises a first mirror electrode 413A, a second mirror electrode 413B, and a third mirror electrode 413C. Electrons of the particle beam which are reflected back at the electrostatic mirror 414 once again travel along the second optical axis OA2 and re-enter the beam deflection device 410. Then, they are deflected to the third optical axis OA3 by the third magnetic sector 411C, the fourth magnetic sector 411D, and the fifth magnetic sector 411E.

The electrons of the particle beam emerge from the beam deflection device 410 and said electrons are guided along the third optical axis OA3 to an object 425 that is intended to be examined and arranged in an object preparation device in the form of a microtome 114. On the path to the object 425, the particle beam is guided to a fifth electrostatic lens 418, a beam-guiding tube 420, a fifth multi-pole unit 418A, a sixth multi-pole unit 418B, and an objective lens 421. The fifth electrostatic lens 418 is an electrostatic immersion lens. By way of the fifth electrostatic lens 418, the particle beam is decelerated or accelerated to an electric potential of the beam-guiding tube 420.

In some embodiments, by means of the objective lens 421, the particle beam is focused in a focal plane in which the object 425 is arranged. The microtome 114 is arranged at a movable specimen stage 424. The movable specimen stage 424 is arranged in a specimen chamber 426 of the particle beam apparatus 400. The specimen stage 424 is embodied to be movable in three directions arranged perpendicular to one another, namely in an x-direction (first stage axis), in a y-direction (second stage axis) and in a z-direction (third stage axis). Moreover, the specimen stage 424 can be rotated about two rotational axes which are arranged perpendicular to one another (stage rotation axes).

In some embodiments, the specimen chamber 426 is under vacuum. For the purposes of producing the vacuum, a pump (not illustrated) is arranged at the specimen chamber 426. In the illustrative embodiment illustrated in FIG. 3, the specimen chamber 426 is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the specimen chamber 426 is vacuum-sealed.

The objective lens 421 may be embodied as a combination of a magnetic lens 422 and a sixth electrostatic lens 423. The end of the beam-guiding tube 420 further may be an electrode of an electrostatic lens. After emerging from the beam-guiding tube 420, particles of the particle beam apparatus are decelerated to a potential of the object 425. The objective lens 421 is not restricted to a combination of the magnetic lens 422 and the sixth electrostatic lens 423. Rather, the objective lens 421 may assume any suitable form. By way of example, the objective lens 421 also may be embodied as a purely magnetic lens or as a purely electrostatic lens.

The particle beam which is focused onto the object 425 interacts with the object 425. Interaction particles are generated. In particular, secondary electrons are emitted from the object 425 or backscattered electrons are scattered back at the object 425. The secondary electrons or the backscattered electrons are accelerated again and guided into the beam-guiding tube 420 along the third optical axis OA3. In particular, the trajectories of the secondary electrons and the backscattered electrons extend on the route of the beam path of the particle beam in the opposite direction to the particle beam.

In some embodiments, the particle beam apparatus 400 comprises a first analysis detector 419 which is arranged between the beam deflection device 410 and the objective lens 421 along the beam path. Secondary electrons traveling in directions oriented at a large angle with respect to the third optical axis OA3 are detected by the first analysis detector 419. Backscattered electrons and secondary electrons which have a small axial distance with respect to the third optical axis OA3 at the location of the first analysis detector 419—i.e. backscattered electrons and secondary electrons which have a small distance from the third optical axis OA3 at the location of the first analysis detector 419—enter the beam deflection device 410 and are deflected to a second analysis detector 428 by the fifth magnetic sector 411E, the sixth magnetic sector 411F and the seventh magnetic sector 411G along a detection beam path 427. By way of example, the deflection angle is 90° or 110°.

The first analysis detector 419 generates detection signals which are largely generated by emitted secondary electrons. The detection signals which are generated by the first analysis detector 419 are guided to a monitoring unit 123 and used to obtain information about the properties of the interaction region of the focused particle beam with the object 425. In particular, the focused particle beam is scanned over the object 425 using a scanning device 429. Then, an image of the scanned region of the object 425 can be generated by the detection signals, which are generated by the first analysis detector 419, and it can be displayed on a display unit. The display unit is for example a monitor 124 that is arranged at the monitoring unit 123.

In some embodiments, the second analysis detector 428 is also connected to the monitoring unit 123. Detection signals of the second analysis detector 428 are supplied to the monitoring unit 123 and used to generate an image of the scanned region of the object 425 and to display it on a display unit. The display unit is for example the monitor 124 that is arranged at the monitoring unit 123.

In some embodiments, arranged at the specimen chamber 426 is a radiation detector 500, which is used to detect interaction radiation, for example x-ray radiation and/or cathodoluminescence. The radiation detector 500 is connected to the monitoring unit 123, which has the monitor 124. The monitoring unit 123 processes detection signals of the radiation detector 500 and displays them in the form of images on the monitor 124.

Figure 4:
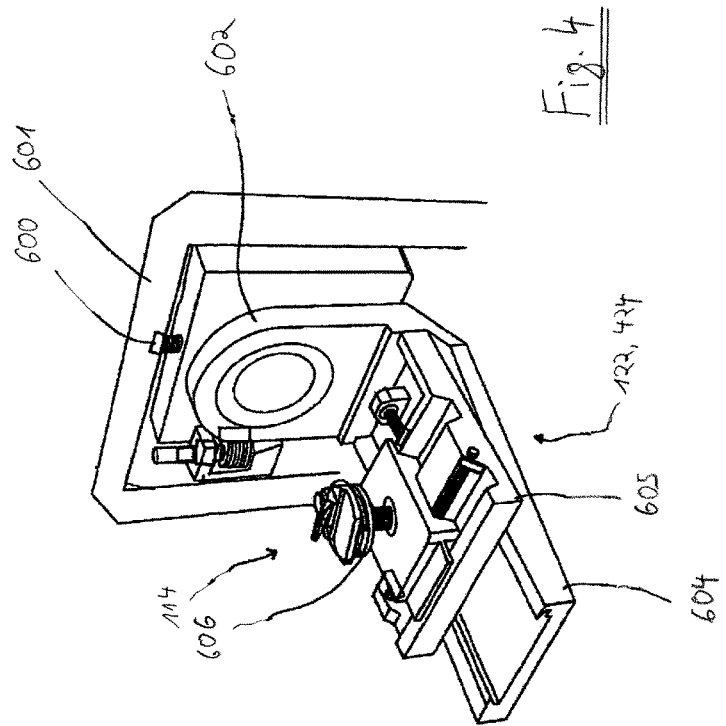
FIG. 4 shows a schematic illustration of an illustrative embodiment of a movably embodied specimen stage for a particle beam apparatus, according to an embodiment of the system described herein.

Now, the specimen stage 122, 424 of the particle beam apparatuses 100, 200 and 400 explained above is discussed in more detail below. In some embodiments, the specimen stage 122, 424 is embodied as a movable specimen stage, which is illustrated schematically in the illustrative embodiments of FIGS. 4 and 5. Reference is made to the fact that the system described herein is not restricted to the specimen stage 122, 424 described here. Rather, the system described herein can have any movable specimen stage that is suitable for the system described herein.

Arranged on the specimen stage 122, 424 is the microtome 114, in which the object 125, 425 is arranged in turn. The specimen stage 122, 424 has movement elements that ensure a movement of the specimen stage 122, 424 in such a way that a region of interest on the object 125, 425 can be examined by means of a particle beam. The movement elements are illustrated schematically in FIGS. 4 and 5 and are explained below.

The specimen stage 122, 424 has a first movement element 600 at a housing 601 of the specimen chamber 120, 201 or 426, in which the specimen stage 122, 424 is arranged. The first movement element 600 facilitates a movement of the specimen stage 122, 424 along the z-axis (third stage axis). Further, provision is made of a second movement element 602. The second movement element 602 facilitates a rotation of the specimen stage 122, 424 about a first stage rotation axis 603, which is also referred to as a tilt axis. This second movement element 602 serves to tilt an object 125, 425 arranged in the microtome 114 about the first stage rotation axis 603.

Arranged at the second movement element 602, in turn, is a third movement element 604 that is embodied as a guide for a carriage and that ensures that the specimen stage 122, 424 is movable in the x-direction (first stage axis). The aforementioned carriage is a further movement element in turn, namely a fourth movement element 605. The fourth movement element 605 is embodied in such a way that the specimen stage 122, 424 is movable in the y-direction (second stage axis). To this end, the fourth movement element 605 has a guide in which a further carriage is guided, the microtome 114 in turn being arranged at the latter.

The microtome 114 is embodied, in turn, with a fifth movement element 606 that facilitates a rotation of the microtome 114 about a second stage rotation axis 607. This second stage rotation axis 607 is oriented perpendicular to the first stage rotation axis 603.

On account of the above-described arrangement, the specimen stage 122, 424 of the illustrative embodiment discussed here has the following kinematic chain: first movement element 600 (movement along the z-axis)—second movement element 602 (rotation about the first stage rotation axis 603)—third movement element 604 (movement along the x-axis)—fourth movement element 605 (movement along the y-axis)—fifth movement element 606 (rotation about the second stage rotation axis 607).

In a further illustrative embodiment (not illustrated here), provision is made of arranging further movement elements at the specimen stage 122, 424 such that movements along further translational axes and/or about further rotational axes are facilitated.

Figure 5:
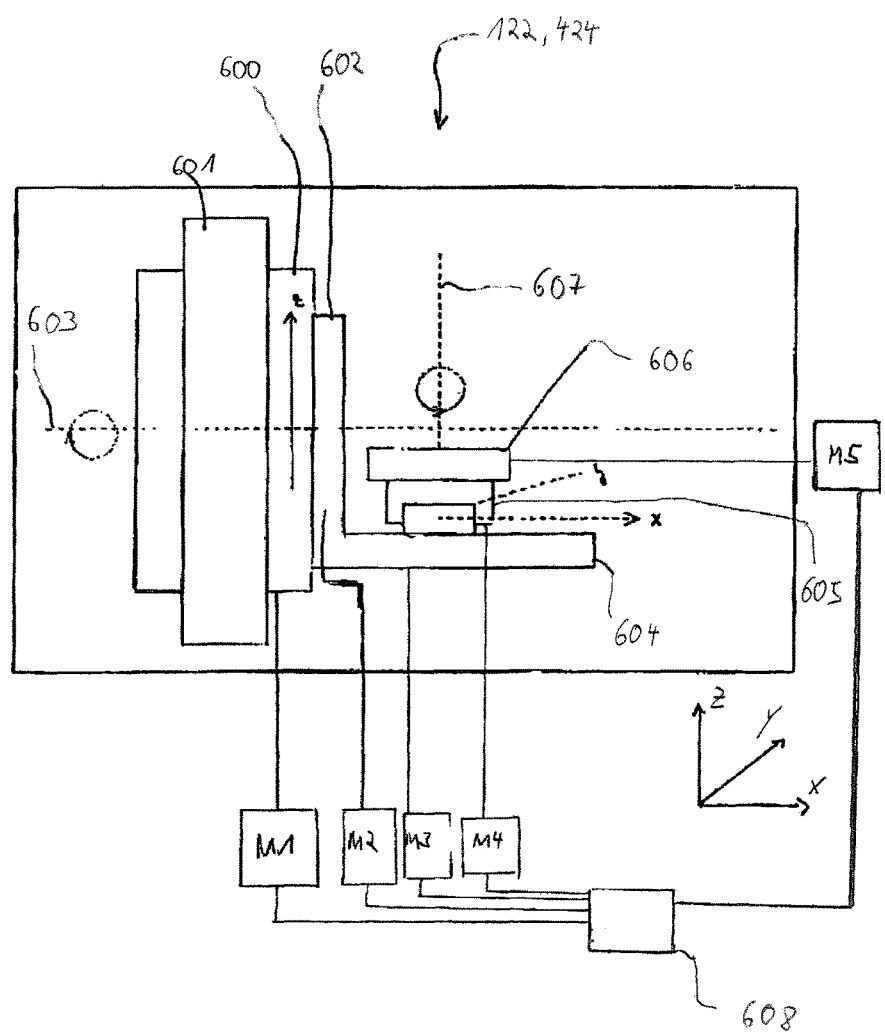
FIG. 5 shows a further schematic illustration of the specimen stage according to FIG. 4, according to an embodiment of the system described herein.

It is clear from FIG. 5 that each of the aforementioned movement elements is connected to a stepper motor. Thus, the first movement element 600 is connected to a first stepper motor M1 and the former is driven on account of a driving force that is provided by the first stepper motor M1. The second movement element 602 is connected to a second stepper motor M2, which drives the second movement element 602. The third movement element 604 is connected, in turn, to a third stepper motor M3. The third stepper motor M3 provides a driving force for driving the third movement element 604. The fourth movement element 605 is connected to a fourth stepper motor M4, wherein the fourth stepper motor M4 drives the fourth movement element 605. Further, the fifth movement element 606 is connected to a fifth stepper motor M5. The fifth stepper motor M5 provides a driving force that drives the fifth movement element 606. The aforementioned stepper motors M1 to M5 are controlled by a control unit 608 (see FIG. 5).

Figure 6:
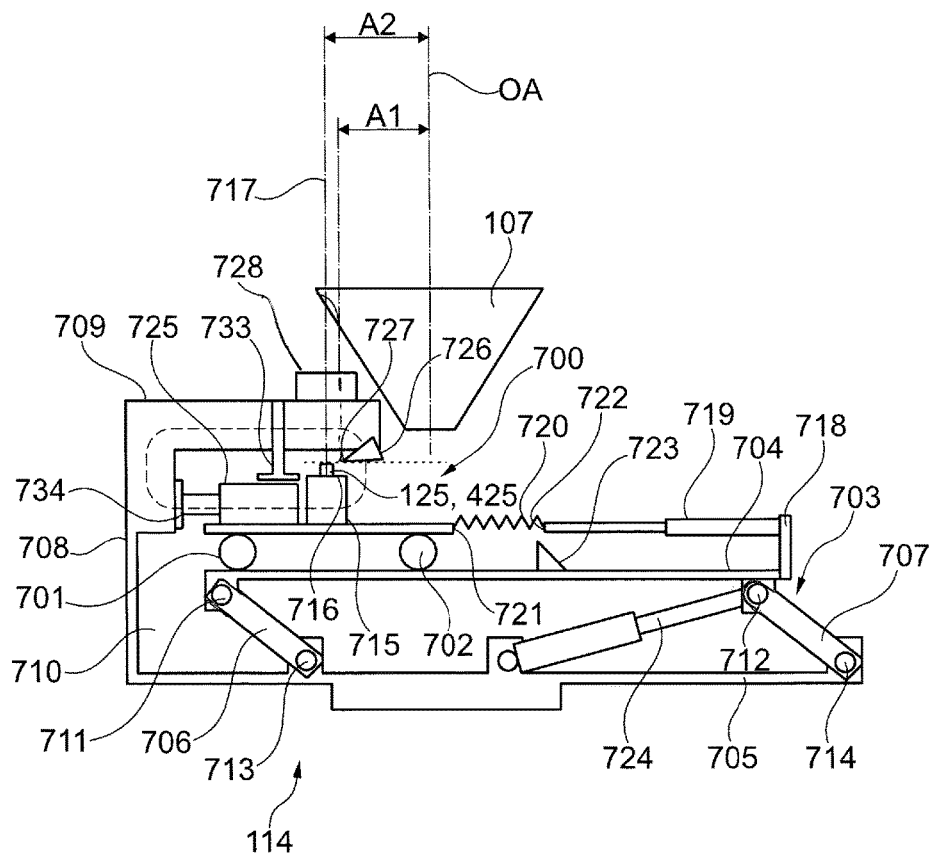
FIG. 6 shows a schematic illustration of an object preparation device in the form of a microtome, according to an embodiment of the system described herein.

FIG. 6 shows a schematic side view of an illustrative embodiment of the object preparation device in the form of the microtome 114, which is arranged in the specimen chamber 120 of the SEM 100, the specimen chamber 201 of the combination apparatus 200 or in the specimen chamber 426 of the particle beam apparatus 400. Therefore, the microtome 114 is an "in situ microtome". The microtome 114 that is arranged in the specimen chamber 120 of the SEM 100 is explained below. FIG. 6 shows the first objective lens 107 of the SEM 100. The optical axis OA extends through the first objective lens 107. A corresponding statement applies to the microtome 114 that is arranged in the specimen chamber 201 of the combination apparatus 200 or the specimen chamber 426 of the particle beam apparatus 400.

The microtome 114 illustrated in FIG. 6 has an object receptacle device 700 that is embodied to be movable in a linear fashion only, with a first roller unit 701 and a second roller unit 702 being arranged thereon. Expressed differently, the object receptacle device 700 itself is embodied in such a way that it can only move itself along one axis. To this end, the object receptacle device 700 of this illustrative embodiment rolls by way of the first roller unit 701 and the second roller unit 702 along a first side 704 of a base unit 703. The system described herein is not restricted to the use of roller units. Rather, any movement appliance by means of which the object receptacle device 700 is linearly movable along one axis is suitable, in particular a linear guide that has a rail.

In a side view, the base unit 703 has the form of a rhomboid. As already mentioned above, the rhomboid is a quadrilateral in which opposite sides are parallel. The base unit 703 has the first side 704, a second side 705, a third side 706 and a fourth side 707. The first side 704 and the second side 705 are arranged opposite and parallel to one another. The third side 706 and the fourth side 707 are arranged opposite and parallel to one another. Further, the first side 704 and the second side 705 in each case have a longer embodiment than the third side 706 and the fourth side 707.

The microtome 114 has a base plate in the form of the second side 705, a first sidewall 708 and a second sidewall 709. The base plate in the form of the second side 705 is arranged at the first sidewall 708 at an angle of 90°. Further, the second sidewall 709 is arranged at the first sidewall 708 at an angle of 90°. The system described herein is not restricted to the aforementioned angles. Rather, use can be made of any angle that is suitable for the system described herein and that differs from 0° and 180°. The base plate in the form of the second side 705 and the second sidewall 709 are spaced apart from one another. The base plate in the form of the second side 705, the first sidewall 708 and the second sidewall 709 include a space 710 in which the object receptacle device 700 can be arranged. This will still be explained below.

The first side 704 of the base unit 703 is connected in articulated fashion to the third side 706 of the base unit 703 by way of a first joint 711. Moreover, the first side 704 of the base unit 703 is connected in articulated fashion to the fourth side 707 of the base unit 703 by way of a second joint 712. The second side 705 of the base unit 703 is connected to the third side 706 of the base unit 703 by way of a third joint 713. Moreover, the second side 705 of the base unit 703 is connected to the fourth side 707 of the base unit 703 by way of a fourth joint 714.

An object receptacle 715 is arranged at the object receptacle device 700. The object receptacle 715 serves to receive the object 125, 425. The object receptacle 715 has a receptacle area 716 for arranging the object 125, 425. Extending through the object receptacle 715 is a receptacle axis 717 that is arranged perpendicular to the receptacle area 716 of the object receptacle 715. Expressed differently, the receptacle axis 717 that extends through the object receptacle 715 is aligned perpendicular to the receptacle area 716 of the object receptacle 715.

A holder 718 is embodied at the first side 704 of the base unit 703. A first linear actuator 719 is arranged, in turn, at the holder 718. A spring element 720 is arranged between the object receptacle device 700 and the first linear actuator 719. The spring element 720 connects the object receptacle device 700 and the first linear actuator 719. To this end, the spring element 720 has a first end 721 and a second end 722. The first end 721 of the spring element 720 is arranged at the object receptacle device 700. The second end 722 of the spring element 720 is arranged at the first linear actuator 719. A stop device 723 for stopping a movement of the object receptacle device 700 along the first side 704 is also arranged at the first side 704 of the base unit 703. This, and the function and mode of operation of the first linear actuator 719 will be discussed further below.

A second linear actuator 724 for rotating the base unit 703 about a first rotation axis of the third joint 713 and about a second rotation axis of the fourth joint 714 is arranged at the base unit 703. The function and the mode of operation of the second linear actuator 724 will be discussed further below.

The first sidewall 708 is embodied as a support wall, against which a third linear actuator 725 is braced, wherein the third linear actuator 725 is arranged at the object receptacle device 700 and embodied to move the object receptacle device 700. A pressure sensor 734 is arranged between the third actuator 725 and the first sidewall 708. The function and the mode of operation of the third linear actuator 725 and of the pressure sensor 734 will be discussed further below.

The microtome 114 has a cutting device 726 in the form of a knife. By way of example, the cutting device 726 is formed from stainless steel, from diamond and/or from sapphire. However, the system described herein is not restricted to the aforementioned materials. Rather, any material that is usable in the object preparation device in the form of the microtome 114 can be used for the cutting device 726. The cutting device 726 has a cutting bevel 727 which, for example, has a planoconcave and/or wedge-shaped embodiment. However, the system described herein is not restricted to the aforementioned shapes of the cutting bevel 727. Rather, any form of the cutting bevel 727 that is suitable for the system described herein can be used.

The microtome 114 also has a cutting device drive 728 for moving the cutting bevel 727. By way of example, the cutting device drive 728 is embodied as a piezo motor which moves the cutting bevel 727 in an oscillating fashion. Both the cutting speed of the cutting bevel 727, by setting a cutting frequency, and the amplitude of the cutting movement of the cutting device 726 are adjustable in the illustrative embodiment. Consequently, an oscillating cutting movement of the cutting bevel 727 that is particularly expedient for removing a layer of the object 125, 425 is provided (namely a sawing movement along the cutting bevel 727).

Figure 7:
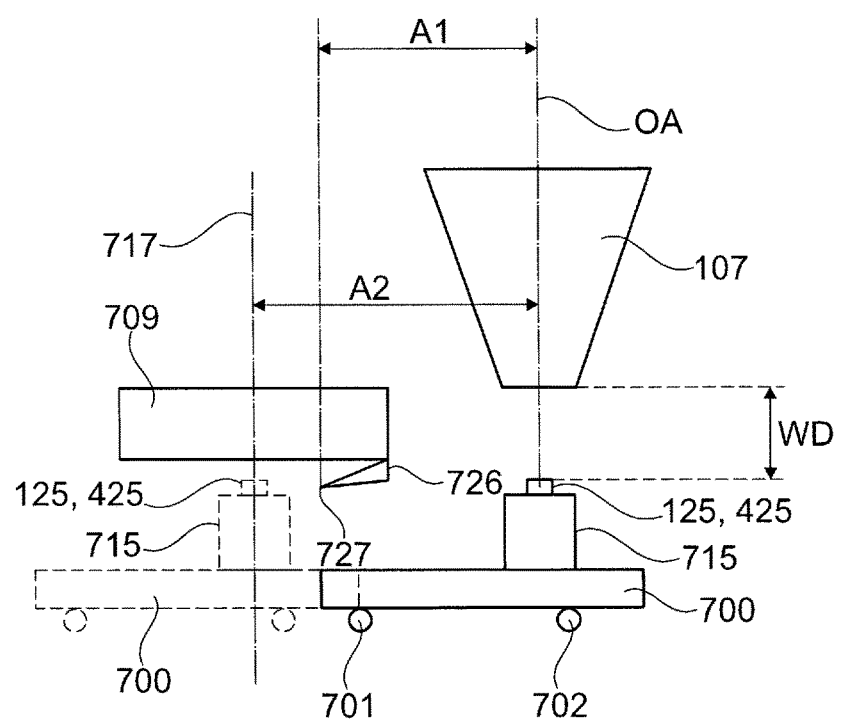
FIG. 7 shows a simplified illustration of the object preparation device according to FIG. 6, according to an embodiment of the system described herein.

In the illustrative embodiment of FIG. 6, the object receptacle device 700 is arranged at a first position, namely at an initial position. Then, the object receptacle device 700 is arranged in the space 710. The object receptacle device 700 adopts this first position before the cutting device 726 cuts a layer off the object 125, 425 during a movement of the object receptacle device 700 from the first position in the direction of the second position. The second position is illustrated in the illustrative embodiment of FIG. 7, wherein FIG. 7 is a simplified illustration of the microtome 114 illustrated in FIG. 6. In contrast to FIG. 6, FIG. 7 only illustrates the second sidewall 709, the cutting device 726, the cutting bevel 727, the first objective lens 107, the optical axis OA, the object receptacle device 700 with the two roller units 701, 702, and the object receptacle 715. When the object 125, 425 is arranged along the optical axis OA, the object receptacle device 700 is arranged at the second position. Expressed differently, the object receptacle device 700 is arranged at the second position when the optical axis OA extends through the object 125, 425. By way of example, the optical axis OA extends substantially through a center of the object 125, 425. The second position is arranged offset to the first position along the axis along which the object receptacle device 700 is moved. In FIG. 7, the first position of the object receptacle device 700 is illustrated using dashed lines. The second position of the object receptacle device 700 is an analysis and/or processing position. The object 125, 425 that is arranged in the object receptacle 715 is able to be analyzed, in particular imaged, and/or processed in the analysis and/or processing position using the primary electron beam of the SEM 100.

The microtome 114 also has an observation axis that extends through the object receptacle 715 when the object receptacle device 700 is arranged at the second position, i.e. at the analysis and/or processing position. In this illustrative embodiment of the microtome 114, the observation axis corresponds to the optical axis OA that extends through the first objective lens 107 of the SEM 100. However, if the object receptacle device 700 is arranged at the first position, the optical axis OA is aligned parallel to the receptacle axis 717 extending through the object receptacle 715.

The cutting bevel 727 and the optical axis OA are arranged spaced apart from one another. Expressed differently, the microtome 114 has a first distance A1 between the cutting bevel 727 and the optical axis OA perpendicular to the optical axis OA. Here, the first distance A1 is determined by the stretch from the outermost edge of the cutting bevel 727 to the optical axis OA in a perpendicular direction to the optical axis OA. Moreover, the cutting bevel 727 has a special orientation. This is because the cutting bevel 727 is directed in the direction of the object receptacle 715 of the object receptacle device 700 when the object receptacle device 700 is arranged at the first position—i.e., at the initial position (see FIGS. 6 and 7). Expressed differently, the cutting bevel 727 of the cutting device 726 points in the direction of the object receptacle 715 of to the object receptacle device 700 when the object receptacle device 700 is arranged at the first position.

When the object receptacle device 700 is arranged at the first position, the object receptacle device 700 is arranged spaced apart from the optical axis OA. Expressed differently, there is a second distance A2 between the object receptacle device 700 arranged at the first position and the optical axis OA, wherein the second distance A2 is a distance between the optical axis OA and the receptacle axis 717 perpendicular to the optical axis OA when the object receptacle device 700 is arranged at the first position.

The first distance A1 between the cutting bevel 727 and the optical axis OA is smaller than the second distance A2 between the optical axis OA and the receptacle axis 717 perpendicular to the optical axis OA when the object receptacle device 700 is arranged at the first position. Expressed differently, the cutting bevel 727 lies closer to the optical axis OA than the object receptacle 715 of the object receptacle device 700 when the object receptacle device 700 is arranged at the first position.

The object receptacle device 700 is configured in such a way that it is movable, firstly, from the first position into the second position and, secondly, from the second position into the first position. This will be explained below.

The third linear actuator 725 serves for the linear movement of the object receptacle device 700 along the first side 704 of the base unit 703. Expressed differently, the third linear actuator 725 produces a force with which a movement of the object receptacle device 700 from the first position in the form of the initial position in the direction of the second position in the form of the analysis and/or processing position is produced. To this end, the third linear actuator 725 braces itself against the first sidewall 708. The object 125, 425 is cut by means of the cutting device 726 during the movement of the object receptacle device 700 from the first position in the direction of the second position. As soon as the cutting process is completed—as soon as a layer of the object 125, 425 has been removed by the cutting device 726—the third linear actuator 725 is stopped. Then, it no longer produces a driving force. It is not mandatory for the object receptacle device 700 to already be situated in the second position when the third linear actuator 725 is stopped. As a rule, the object receptacle device 700 has not yet reached the second position at all when the third linear actuator 725 is stopped.

Then, the further movement of the object receptacle device 700 in the direction of the second position in the form of the analysis and/or processing position is effectuated in this illustrative embodiment by means of the first linear actuator 719, which produces a force in such a way that the object receptacle device 700 is pulled in the direction of the second position and arranged at the second position. To this end, the stop device 723 is also used in the illustrative embodiment illustrated here. By way of example, the stop device 723 is arranged in such a way that the object receptacle device 700 is arranged at the second position when the stop device 723 is touched by the object receptacle device 700. Therefore, the movement of the object receptacle device 700 from the first position in the direction of the second position is stopped as soon as the object receptacle device 700 touches the stop device 723. There can be a further movement of the first linear actuator 719 without the object receptacle device 700 being moved further on account of the spring element 720. Consequently, there is no movement of the object receptacle device 700 beyond the second position.

In a further embodiment, the stop device 723 serves to stop the movement of the object receptacle device 700 without the object receptacle device 700 already being situated in the second position. In this embodiment, the object receptacle device 700 is moved into the second position, for example by a movement of the base unit 703 or of the specimen stage 122, 424 on which the microtome 114 is arranged, as soon as the object receptacle device 700 rests against the stop device 723.

In the illustrative embodiment of FIG. 6, the first linear actuator 719 and the third linear actuator 725 have different functions. The third linear actuator 725 serves for the movement of the object receptacle device 700 away from the first position, until the cutting process is completed. By contrast, the first linear actuator 719 serves for the movement of the object receptacle device 700 after the cutting process, to be precise until the object receptacle device 700 is arranged at the second position, for example.

The second linear actuator 724 likewise has a special function and mode of operation. The second linear actuator 724 is used to rotate the base unit 703 about a first rotation axis of the third joint 713 and about a second rotation axis of the fourth joint 714. As a result of this, the first side 704 is displaced parallel to the second side 705 along the optical axis OA. In this way, the distance between the area of the object 125, 425 that is arranged on the object receptacle 715 and exposed after the cutting process and the first objective lens 107 of the SEM 100 (i.e. the working distance WD) is set, for example. Consequently, it is possible to always position the exposed area in such a way that the working distance WD between the exposed area and the first objective lens 107 is constant (see FIG. 7). Therefore, renewed focusing of the first objective lens 107 onto an exposed area after the cutting process is not mandatory. Expressed differently, the base unit 703 is movably guided along the third axis in the form of the z-axis by way of the rotation of the base unit 703 about the first rotation axis of the third joint 713 and about the second rotation axis of the fourth joint 714. By way of example, the third axis is aligned parallel to the observation axis or said third axis corresponds to the observation axis. By way of example, the working distance WD lies in the range from 1 mm to 5 mm, including the range boundaries. However, the system described herein is not restricted to this range. Instead, any working distance that is suitable for the system described herein can be selected. Additionally, or as an alternative thereto, the base unit 703 serves to set the height of the object receptacle apparatus 700 in such a way that the distance of the object 125, 425 from the cutting bevel 727 is always constant. As a result of this, it is possible to successively ablate layers with an identical layer thickness using the cutting bevel 727 without modifying the height position of the cutting bevel 727. Expressed differently, the height position of the cutting bevel 727 is constant. By way of example, the height corresponds to a perpendicular distance between the plane of the second side 705 and the cutting bevel 727 along the observation axis, for example the optical axis OA.

The pressure ascertained by the pressure sensor 734 can be converted into an exerted force. The pressure sensor 734 cooperates with the third linear actuator 725. By way of example, the pressure sensor 734 serves to obtain data for future applications of the microtome 114. When moving the object receptacle device 700 with the object 125, 425 in the direction of the cutting bevel 727, the object 125, 425 strikes the cutting bevel 727. As a result of this, a force is exerted on the object 125, 425 by means of the cutting bevel 727. Now, it may be the case that the cutting process is not acceptable in the case of a force that is too high or a force that is too low. By way of example, the cutting process may be incomplete or the object 125, 425 may be damaged. In both cases, the quality of the exposed area is possibly only suitable to a restricted extent for imaging and/or for further analysis by means of a particle beam. By determining the force by means of measuring the pressure using the pressure sensor 734 and by determining the quality of the imaging of the exposed areas that was obtained, it is possible to ascertain a force that is sufficient for the cutting process in such a way that the exposed areas are well suited to imaging and/or a further analysis using the particle beam. This ascertained force is then also used in future for ablating material of the object 125, 425. Further, the pressure sensor 734 has the function of determining the distance of the object 125, 425 from the cutting bevel 727. By way of example, there may be a so-called dummy cut at the start of each examination of an object 125, 425, during which the object 125, 425 is moved toward the cutting bevel 727 but no layer of the object 125, 425 is removed by the cutting bevel 727 as the latter does not touch the object 125, 425 during the movement of the object 125, 425 in the direction of the cutting bevel 727. This is determinable by means of the pressure sensor 734 since the force determined by means of the pressure sensor 734 does not change in that case. In this case, the object 125, 425 is moved in the direction of the cutting bevel 727 by means of the base unit 703 and/or the specimen stage 122, 424, for example. Then, there is, once again, a movement of the object receptacle device 700 together with the object 125, 425 in the direction of the cutting bevel 727, for example. If the cutting bevel 727 now strikes the object 125, 425, this is indicated by an increased pressure at the pressure sensor 734. In an even further embodiment, the pressure sensor 734 is used to ascertain properties of the object 125, 425. By way of example, if the object 125, 425 is provided with hard inclusions that render a removal of a layer impossible, these inclusions are ascertained, by means of the pressure sensor 734, by way of a force to be applied to the object 125, 425 being exceeded. The same applies if the cutting bevel 727 only strikes the object receptacle device 700 but not the object 125, 425 itself, for example. This can likewise be ascertained by a certain force being exceeded by way of a measurement by means of the pressure sensor 734.

The microtome 114 has a sensor 733 for measuring the distance of the object receptacle device 700 from the cutting bevel 727. By way of example, the sensor 733 is embodied as a capacitive distance sensor. As a result of this, it is possible, in particular, to monitor the movement of the object receptacle device 700 along the optical axis OA and/or to set the position of the object receptacle device 700 along the optical axis OA by monitoring the rotational movement of the base unit 703. In this way, it is possible to determine the distance of the object 125, 425 from the cutting bevel 727, as already explained above.

Figure 8A:
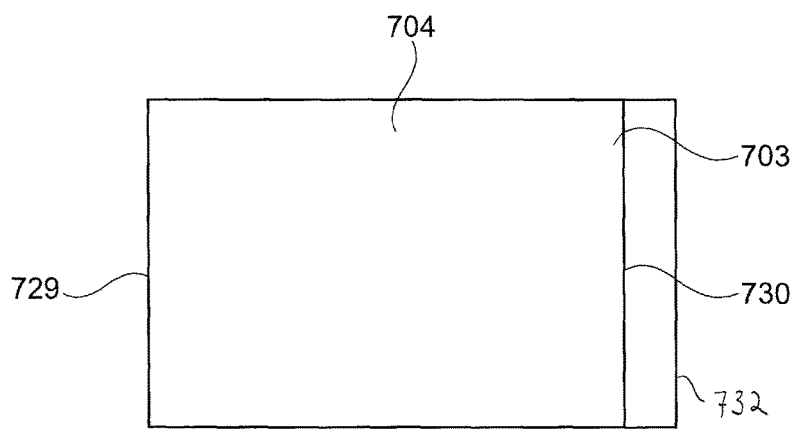
FIG. 8A shows a plan view of a base unit of an object preparation device, according to an embodiment of the system described herein.
Figure 8B:
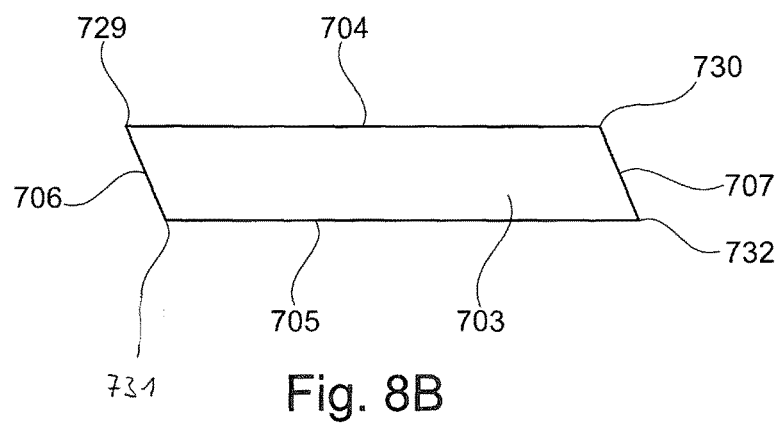
FIG. 8B shows a side view of the base unit according to FIG. 8A, according to an embodiment of the system described herein.

FIGS. 8A and 8B show an illustrative embodiment of a further base unit 703, which has an integral embodiment. FIG. 8A shows a plan view of the further base unit 703 from above, i.e. proceeding from the first objective lens 107 along the optical axis OA, for example. FIG. 8B shows a side view of the further base unit 703. The further base unit 703 also has four sides, namely a first side 704, a second side 705, a third side 706 and a fourth side 707. The first side 704 and the second side 705 are arranged opposite and parallel to one another. The third side 706 and the fourth side 707 are arranged opposite and parallel to one another. The first side 704 and the second side 705 in each case have a longer embodiment than the third side 706 and the fourth side 707. In the side view, the further base unit 703 has the form of a rhomboid.

The first side 704 of the further base unit 703 is connected in integral fashion to the third side 706 at a first border region 729 between the first side 704 and the third side 706. The first border region 729 is a region at which the first side 704 and the third side 706 touch. The first border region 729 of the further base unit 703 is embodied as a first flexure bearing. The first flexure bearing permits relative movement between the first side 704 and the third side 706 by bending.

Moreover, the first side 704 is connected in integral fashion to the fourth side 707 at a second border region 730 between the first side 704 and the fourth side 707. The second border region 730 is a region at which the first side 704 and the fourth side 707 touch. The second border region 730 is embodied as a second flexure bearing. The second flexure bearing permits relative movement between the first side 704 and the fourth side 707 by bending.

The second side 705 is connected in integral fashion to the third side 706 at a third border region 731 between the second side 705 and the third side 706. The third border region 731 is a region at which the second side 705 and the third side 706 touch. The third border region 731 is embodied as a third flexure bearing. The third flexure bearing permits relative movement between the second side 705 and the third side 706 by bending.

Moreover, the second side 705 is connected in integral fashion to the fourth side 707 at a fourth border region 732 between the second side 705 and the fourth side 707. The fourth border region 732 is a region at which the second side 705 and the fourth side 707 touch. The fourth border region 732 is embodied as a fourth flexure bearing. The fourth flexure bearing permits relative movement between the second side 705 and the fourth side 707 by bending.

The further base unit 703, in particular, facilitates a quite low installation height of the object preparation device according to the system described herein in the form of the microtome 114 while simultaneously providing a sufficiently long adjustment travel for good positioning of the object receptacle device 700 that is arranged at the base unit 703 relative to the cutting bevel 727 and/or relative to the first objective lens 107 of the SEM 100. As a result of the low installation height, the adjustment travel of the specimen stage 122 along the optical axis OA is sufficiently good to set an acceptable working distance WD between an exposed area and the first objective lens 107.

Figure 9:
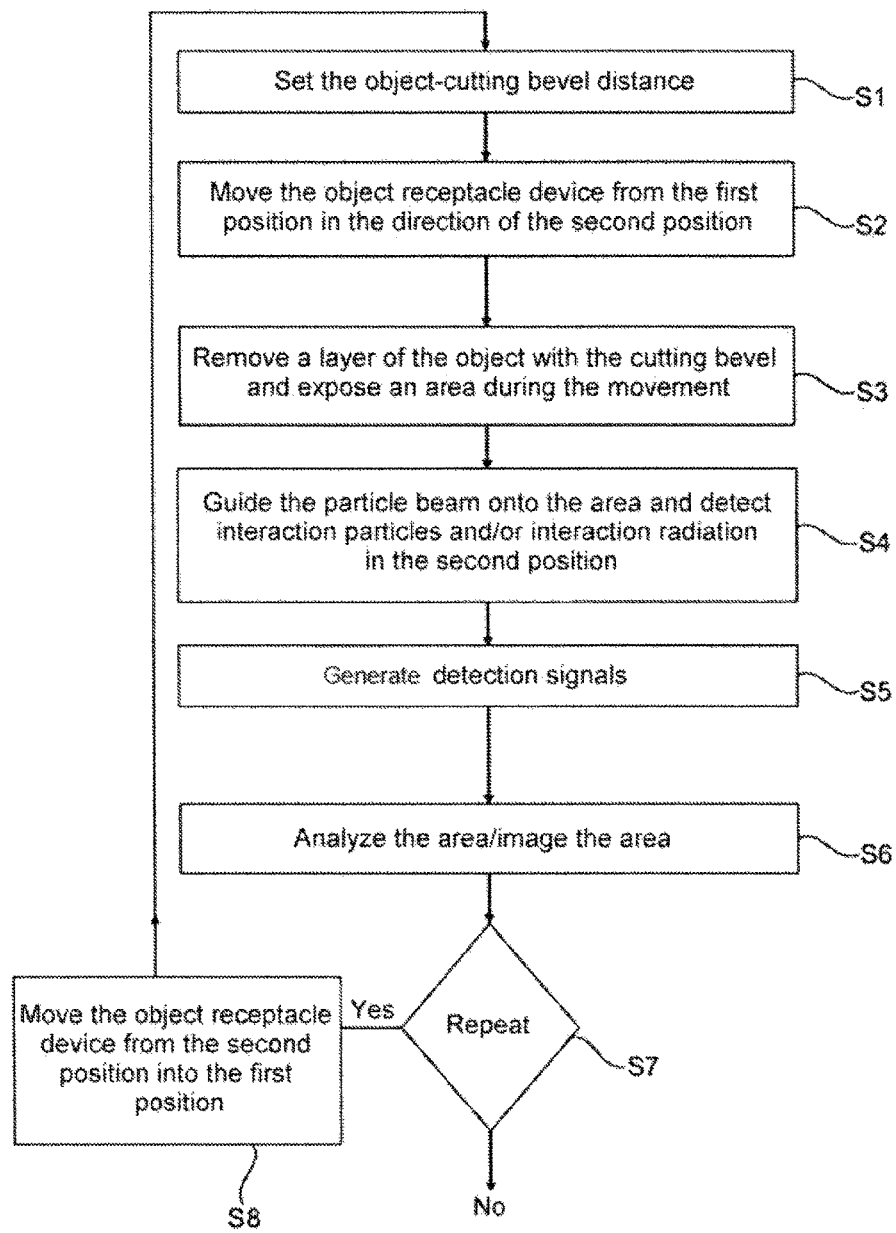
FIG. 9 shows an illustrative embodiment of a method for operating a particle beam apparatus, according to an embodiment of the system described herein.

FIG. 9 shows an illustrative embodiment of a method according to the system described herein for operating the particle beam apparatus in the form of the SEM 100, of the combination apparatus 200 or of the particle beam apparatus 400, wherein the particle beam apparatus 100, 200 or 400 has the above-described object preparation device in the form of the microtome 114. The method is explained in an illustrative fashion below on the basis of the operation of the SEM 100. Corresponding statements apply in respect of the methods for operating the further particle beam apparatuses 200 and 400.

In a method step S1, the distance between the object 125, 425 and the cutting bevel 727 is set on account of the movement of the second linear actuator 724. By way of example, this is carried out by rotating the base unit 703 about the first rotation axis of the third joint 713 and about the second rotation axis of the fourth joint 714. If use is made of the aforementioned further base unit 703, then the further base unit 703 is rotated about a first joint axis of the third border region 731 and about a second joint axis of the fourth border region 732. As a result of this, the distance between the object 125, 425 arranged at the object receptacle 715 and the cutting bevel 727 is set. Consequently, it is possible to always arrange the object 125, 425 at a constant distance from the cutting bevel 727, as already explained above. In a method step S2, the object receptacle device 700 is moved from the first position in the direction of the second position. This is initially performed by actuating the third linear actuator 725, which moves the object receptacle device 700 in linear fashion along the first side 704 of the base unit 703. To this end, the third linear actuator 725 braces itself against the first sidewall 708, for example. The object 125, 425 is cut by means of the cutting device 726 during the movement of the object receptacle device 700 from the first position in the direction of the second position. As soon as the cutting process is completed, a layer of the object 125, 425 was removed using the cutting device 726. An area of the object 125, 425 is exposed during the cutting process (method step S3). Then, the third linear actuator 725 is stopped. The further movement of the object receptacle device 700 in the direction of the second position is then performed by means of the first linear actuator 719. The primary electron beam of the SEM 100 is guided onto the exposed area when the object receptacle device 700 is situated in the second position. The primary electron beam interacts with the exposed area. The interaction particles and/or the interaction radiation arises/arise during the interaction. The interaction particles and/or the interaction radiation are detected by means of at least one of the detectors 116, 117, 119, 121 and 500 (method step S4). Then, detection signals are generated by at least one of the detectors 116, 117, 119, 121 and 500 in method step S5. The exposed area is analyzed in method step S6 by imaging the exposed area. Consequently, an image of the exposed area is generated, said image being stored in a memory (not illustrated here), for example. In the method step S7, there is a query as to whether the method steps S1 to S6 should be repeated. If method steps S1 to S6 are intended to be repeated, the object receptacle device 700 is first of all moved from the second position to the first position in a method step S8. To this end, use is made of the first linear actuator 719 or a superposition of the movements of the first linear actuator and the third linear actuator, for example. As soon as the object receptacle device 700 is arranged at the first position, method steps S1 to S7 are repeated. If carrying out the method steps S1 to S6 again is not desired in method step S7, the method according to the system described herein is stopped.

As explained, the aforementioned method steps S1 to S6 can be repeated multiple times in succession in order, repeatedly, to expose areas anew, which are then examined and imaged using the primary electron beam of the SEM 100. In this way, one image or a plurality of images is/are generated in each case of each exposed area. The generated images can be used to create a 3D reconstruction of the object 125, 425.

Figure 10:
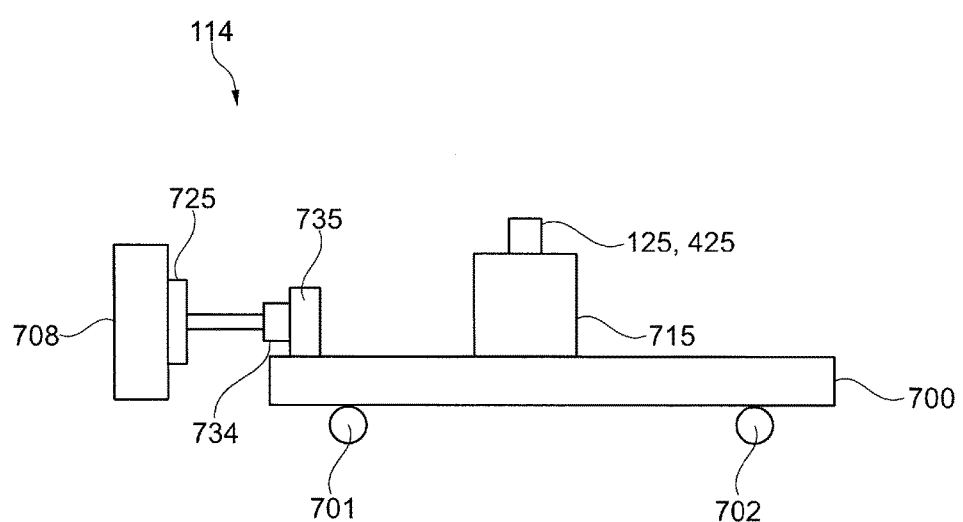
FIG. 10 shows a simplified illustration of a further object preparation device, according to an embodiment of the system described herein.

FIG. 10 shows a simplified illustration of a further illustrative embodiment of a microtome 114. The microtome 114 illustrated in FIG. 10 is based on the microtome 114 of FIG. 6. In contrast to FIG. 6, FIG. 10 only illustrates the first sidewall 708, the object receptacle device 700 with the two roller units 701, 702, and the object receptacle 715. In contrast to the illustrative embodiment of FIG. 6, the third linear actuator 725 is arranged at the first sidewall 708. The third linear actuator 725 braces itself against a support device 735 of the object receptacle device 700. The pressure sensor 734 is arranged between the third actuator 725 and the support device 735. To be precise, the pressure sensor 734 is arranged at the support device 735. The pressure sensor 734 has the same properties as already described above. The third linear actuator 725 brings about the movements of the object receptacle device 700.

Figure 11:
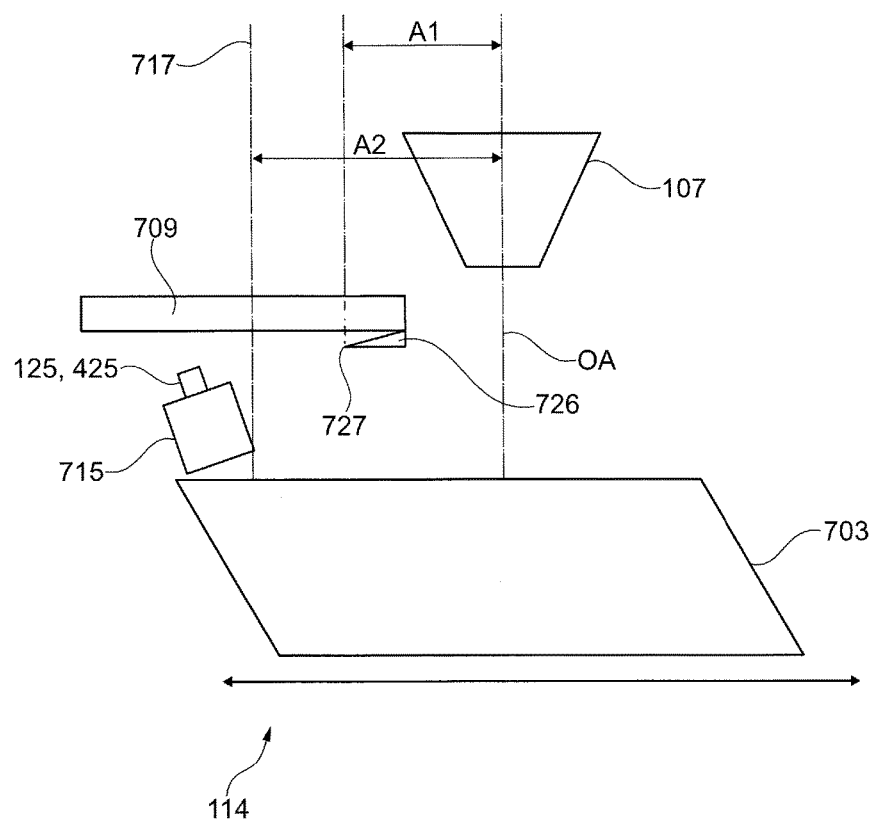
FIG. 11 shows a simplified illustration of yet a further object preparation device, according to an embodiment of the system described herein.

FIG. 11 shows a simplified illustration of a yet further illustrative embodiment of the microtome 114. The microtome 114 illustrated in FIG. 11 is based on the microtome 114 of FIG. 6. In contrast to FIG. 6, the object receptacle 715 of the object receptacle device 700 is arranged directly at the base unit 703 in FIG. 11. Additionally, the base unit 703 has a movable embodiment in the direction of the arrow. In this illustrative embodiment of the microtome 114, provision is made for the object receptacle device 700, i.e. the object receptacle 715, to be moved along a circular trajectory by means of the base unit 703. Additionally, the object 125, 425 can be brought into the first position and into the second position by means of a movement of the base unit 703 in the direction of the arrow. The receptacle axis 717 is aligned parallel to the observation axis in the form of the optical axis OA. The receptacle axis 717 touches the object receptacle device 700, more precisely the object receptacle 715. Further, the observation axis in the form of the optical axis OA is arranged on a first side of the cutting bevel 727, wherein the first side is arranged in a first direction. The receptacle axis 717 is arranged in a second direction when the object receptacle device 700 is arranged in the first position. The first direction and the second direction are diametric. Expressed differently, the first side and the second side are arranged opposite one another such that the observation axis in the form of the optical axis OA and the receptacle axis 717 are also arranged opposite one another when the object receptacle device 700 is arranged in the first position. Then, the cutting bevel 727 is arranged between the observation axis in the form of the optical axis OA and the receptacle axis 717.

The features of the system described herein disclosed in the present description, in the drawings and in the claims may be essential for the realization of the system described herein in the various embodiments thereof, both individually and in arbitrary combinations. The system described herein is not restricted to the described embodiments. It may be varied within the scope of the claims, taking into account the knowledge of the relevant person skilled in the art. Other embodiments of the invention will be apparent to those skilled in the art from a consideration of the specification and/or an attempt to put into practice the invention disclosed herein. It is intended that the specification and examples be considered as illustrative only, with the true scope and spirit of the invention being indicated by the following claims.

The invention claimed is:

1. An object preparation device for preparing an object in a particle beam apparatus, having:
    at least one cutting device;
    at least one cutting bevel for cutting the object; wherein the cutting bevel is arranged at the cutting device;
    at least one movably embodied object receptacle device having an object receptacle for receiving the object; and
    at least one drive unit for moving the object receptacle device from a first position of the object receptacle device into a second position of the object receptacle device;
wherein:
    the first position of the object receptacle device is an initial position;
    the second position of the object receptacle device is an analysis and/or processing position of the object receptacle device;
    an observation axis (OA) extends through the object receptacle when the object receptacle device is arranged at the second position;
    the observation axis (OA) is aligned parallel to a receptacle axis at least touching the object receptacle device when the object receptacle device is arranged at the first position;

the observation axis (OA) is arranged on a first side of the cutting bevel, wherein the first side is arranged in a first direction;

the receptacle axis is arranged on a second side of the cutting bevel, wherein the second side is arranged in a second direction and wherein the first direction and the second direction are diametric;

the cutting bevel is spaced apart from the observation axis (OA) by a first distance (A1), wherein the first distance (A1) is provided by the stretch between the cutting bevel and the observation axis (OA) perpendicular to the observation axis (OA);

the cutting bevel is directed in the direction of the object receptacle of the object receptacle device when the object receptacle device is arranged at the first position;

the object receptacle device arranged at the first position is spaced apart from the observation axis (OA) by a second distance (A2), wherein the second distance (A2) is provided by a stretch between the observation axis (OA) and the receptacle axis perpendicular to the observation axis (OA); and the first distance (A1) is smaller than the second distance (A2).

2. The object preparation device as claimed in claim 1, wherein the object receptacle device is embodied to be movable in a linear fashion only.

3. The object preparation device as claimed in claim 1, wherein the object receptacle has a receptacle area for the object and the object preparation device has at least one of the following features:

the receptacle axis extends through the object receptacle and is arranged perpendicular to the receptacle area of the object receptacle; and the observation axis (OA) is arranged perpendicular to the receptacle area of the object receptacle.

4. The object preparation device as claimed in claim 1, wherein the object preparation device is mountable on a movably embodied specimen stage of the particle beam apparatus.

5. The object preparation device as claimed in claim 1, wherein the object preparation device has the following features:

the object receptacle device is embodied to be movable along a first axis;

at least one base unit, on which the object receptacle device is arranged, wherein the base unit is embodied to be rotatable about a second axis and wherein the second axis is aligned perpendicular to the first axis.

6. The object preparation device as claimed in claim 5, wherein the base unit is guidable in a movable fashion along a third axis (OA), wherein the third axis (OA) is aligned perpendicular to both the first axis and the second axis.

7. The object preparation device as claimed in claim 5, wherein the base unit has a rhomboid-shaped embodiment;

the base unit has a first side, a second side, a third side and a fourth side;

the first side and the second side are arranged opposite and parallel to one another;

the third side and the fourth side are arranged opposite and parallel to one another; and wherein the first side and the second side in each case have a longer embodiment than the third side and the fourth side.

8. The object preparation device as claimed in claim 7, wherein the base unit has at least one of the following features:

(i) the first side is connected in articulated fashion to the third side and the fourth side;

(ii) the second side is connected in articulated fashion to the third side and the fourth side;

(iii) the first side is connected in integral fashion to the third side at a first border region between the first side and the third side, wherein the first border region is embodied as a first flexure bearing;

(iv) the first side is connected in integral fashion to the fourth side at a second border region between the first side and the fourth side, wherein the second border region is embodied as a second flexure bearing;

(v) the second side is connected in integral fashion to the third side at a third border region between the second side and the third side, wherein the third border region is embodied as a third flexure bearing;

(vi) the second side is connected in integral fashion to the fourth side at a fourth border region between the second side and the fourth side, wherein the fourth border region is embodied as a fourth flexure bearing.

9. The object preparation device as claimed in claim 7, wherein the object receptacle device is arranged at the first side.

10. The object preparation device as claimed in claim 5, wherein:

a holder is embodied at the base unit;

a first linear actuator is arranged at the holder; and at least one spring element is arranged between the object receptacle device and the first linear actuator, wherein the spring element connects the object receptacle device and the first linear actuator.

11. The object preparation device as claimed in claim 5, wherein a second linear actuator for rotating the base unit about the second axis is arranged at the base unit.

12. The object preparation device as claimed in claim 1, wherein:

the object preparation device has a support wall; and at least one third linear actuator is arranged at the object receptacle device, said at least one third linear actuator bracing itself against the support wall for the purposes of moving the object receptacle device.

13. The object preparation device as claimed in claim 1, wherein:

the object preparation device has a wall, at which a third linear actuator is arranged; and at least one support device is arranged on the object receptacle device, the third linear actuator bracing itself against said support device for the purposes of moving the object receptacle device.

14. The object preparation device as claimed in claim 1, wherein the object preparation device has at least one pressure sensor (734) for the purposes of ascertaining a force that is exerted by the cutting bevel on the object.

15. The object preparation device as claimed in claim 1, wherein:

the object preparation device has at least one base plate, at least one first sidewall and at least one second sidewall;

the base plate is arranged at the first sidewall at an angle that differs from 0° and 180°;

the second sidewall is arranged at the first sidewall at an angle that differs from 0° and 180°;

the base plate and the second sidewall are arranged at a distance from one another; and the base plate, the first sidewall and the second sidewall include a space in which the object receptacle device is arranged when the object receptacle device is arranged at the first position.

16. The object preparation device as claimed in claim 1, wherein the object preparation device has at least one of the following features:
   at least one sensor for measuring the distance of the object receptacle device from the sensor; and
   at least one cutting device drive (728) for moving the cutting bevel.

17. A particle beam apparatus for analyzing and/or for processing an object, having:
   at least one beam generator for generating a particle beam comprising charged primary particles;
   at least one objective lens for focusing the particle beam onto the object wherein interaction particles and/or interaction radiation arise/arises during an interaction of the particle beam with the object;
   at least one optical axis (OA, OA1, OA2, OA3), along which the particle beam is guidable in the particle beam apparatus;
   at least one detector for detecting the interaction particles and/or the interaction radiation; and
   at least one object preparation device, for preparing an object in the particle beam apparatus having:
      at least one cutting device;
      at least one cutting bevel for cutting the object, wherein the cutting bevel is arranged at the cutting device;
      at least one movably embodied object receptacle device having an object receptacle for receiving the object; and
      at least one drive unit for moving the object receptacle device from a first position of the object receptacle device into a second position of the object receptacle device, wherein
         the first position of the object receptacle device is an initial position,
         the second position of the object receptacle device is an analysis and/or processing position of the object receptacle device,
         an observation axis (OA) extends through the object receptacle when the object receptacle device is arranged at the second position,
         the observation axis (OA) is aligned parallel to a receptacle axis at least touching the object receptacle device when the object receptacle device is arranged at the first position,
         the observation axis (OA) is arranged on a first side of the cutting bevel, wherein the first side is arranged in a first direction,
         the receptacle axis is arranged on a second side of the cutting bevel, wherein the second side is arranged in a second direction and wherein the first direction and the second direction are diametric,
         the cutting bevel is spaced apart from the observation axis (OA) by a first distance (A1), wherein the first distance (A1) is provided by the stretch between the cutting bevel and the observation axis (OA) perpendicular to the observation axis,
         the cutting bevel is directed in the direction of the object receptacle of the object receptacle device when the object receptacle device is arranged at the first position,
         the object receptacle device arranged at the first position is spaced apart from the observation axis (OA) by a second distance (A2), wherein the second distance (A2) is provided by a stretch between the observation axis (OA) and the receptacle axis perpendicular to the observation axis, and the first distance (A1) is smaller than the second distance (A2),
      wherein the observation axis (OA) of the object preparation device corresponds to the optical axis (OA, OA1, OA2, OA3) of the particle beam apparatus.

18. The particle beam apparatus as claimed in claim 17, wherein the particle beam apparatus has one of the following features:
   the object preparation device is arranged at a movably embodied specimen stage of the particle beam apparatus, wherein the specimen stage is embodied to be movable along a first stage axis (x-axis), a second stage axis (y-axis) and a third stage axis (z-axis), wherein the first stage axis (x-axis), the second stage axis (y-axis) and the third stage axis (z-axis) are aligned perpendicular to one another; and
   the object preparation device is arranged at a movably embodied specimen stage of the particle beam apparatus, wherein the specimen stage is embodied to be movable along a first stage axis (x-axis), a second stage axis (y-axis) and a third stage axis (z-axis), wherein the first stage axis (x-axis), the second stage axis (y-axis) and the third stage axis (z-axis) are aligned perpendicular to one another, wherein the specimen stage is embodied to be rotatable about a first stage rotation axis and/or about a second stage rotation axis, wherein the first stage rotation axis is aligned perpendicular to the second stage rotation axis.

19. The particle beam apparatus as claimed in claim 17, wherein the particle beam apparatus has at least one mirror corrector for correcting chromatic and/or spherical aberration.

20. The particle beam apparatus as claimed claim 17, wherein the particle beam apparatus is designed as an electron beam apparatus and/or as an ion beam apparatus.

21. The particle beam apparatus as claimed in claim 17, wherein the beam generator for generating the particle beam comprising charged primary particles is embodied as a first beam generator for generating a first particle beam comprising first charged primary particles and the objective lens is embodied as a first objective lens for focusing the first particle beam, and wherein the particle beam apparatus furthermore has:
   at least one second beam generator for generating a second particle beam comprising second charged primary particles; and
   at least one second objective lens for focusing the second particle beam onto the object.

22. A method for operating a particle beam apparatus for analyzing and/or for processing an object, having at least one beam generator for generating a particle beam comprising charged primary particles, at least one objective lens for focusing the particle beam onto the object, wherein interaction particles and/or interaction radiation arise/arises during an interaction of the particle beam with the object, at least one optical axis (OA, OA1, OA2, OA3), along which the particle beam is guidable in the particle beam apparatus, at least one detector for detecting the interaction particles and/or the interaction radiation, and at least one object preparation device, for preparing an object in the particle beam apparatus having at least one cutting device, at least one cutting bevel for cutting the object, wherein the cutting bevel is arranged at the cutting device, at least one movably embodied object receptacle device having an object receptacle for receiving the object, and at least one drive unit for moving the object receptacle device from a first position of the object receptacle device into a second position of the object receptacle device, wherein the first position of the object receptacle device is an initial position, the second position of the object receptacle device is an analysis and/or processing position of the object receptacle device, an observation axis (OA) extends through the object receptacle when the object receptacle device is arranged at the second position, the observation axis (OA) is aligned parallel to a receptacle axis at least touching the object receptacle device when the object receptacle device is arranged at the first position, the observation axis (OA) is arranged on a first side of the cutting bevel, wherein the first side is arranged in a first direction, the receptacle axis is arranged on a second side of the cutting bevel, wherein the second side is arranged in a second direction and wherein the first direction and the second direction are diametric, the cutting bevel is spaced apart from the observation axis (OA) by a first distance (A1), wherein the first distance (A1) is provided by the stretch between the cutting bevel and the observation axis (OA) perpendicular to the observation axis, the cutting bevel is directed in the direction of the object receptacle of the object receptacle device when the object receptacle device is arranged at the first position, the object receptacle device arranged at the first position is spaced apart from the observation axis (OA) by a second distance (A2), wherein the second distance (A2) is provided by a stretch between the observation axis (OA) and the receptacle axis perpendicular to the observation axis, and the first distance (A1) is smaller than the second distance (A2), wherein the observation axis (OA) of the object preparation device corresponds to the optical axis (OA, OA1, OA2, OA3) of the particle beam apparatus, the method including the following steps:

setting a relative distance of the object from the cutting bevel;

moving the object receptacle device from the first position in the direction of the second position, wherein a layer of the object is removed by the cutting bevel when moving the object receptacle device such that an area of the object is exposed;

supplying the particle beam to the exposed area;

detecting the interaction particles and/or the interaction radiation and generating detection signals; and analyzing the exposed area by means of the detection signals.

23. The method as claimed in claim 22, including the following step:

at least one part of the base unit is rotated about the second axis for the purposes of setting the relative distance of the object from the cutting bevel.

24. A particle beam apparatus for analyzing and/or for processing an object, having:

a specimen chamber;

at least one particle-optical column for generating and guiding a particle beam comprising charged primary particles, wherein the particle-optical column defines an optical axis (OA, OA1, OA2, OA3), along which the particle beam is guidable in the particle beam apparatus from a particle beam generator to the specimen chamber;

at least one detector for detecting interaction particles and/or the interaction radiation of an interaction of the particle beam with the object; and at least one object preparation device having a cutting device, which has a cutting bevel, and an object receptacle for receiving the object, wherein:

the object receptacle is embodied to be movable in a plane substantially perpendicular to the optical axis (OA, OA1, OA2, OA3) of the particle-optical column; and the cutting device is aligned in such a way that the cutting bevel of which extends in a plane that is aligned parallel to the plane substantially perpendicular to the optical axis (OA, OA1, OA2, OA3) of the particle-optical column and is arranged at the cutting device at a side distant from the optical axis (OA, OA1, OA2, OA3) of the particle-optical column.

25. An object preparation device for preparing an object in a particle beam apparatus, having:

a cutting device that has a cutting bevel;

an object receptacle for receiving the object, wherein the object receptacle is adjustable along a linear trajectory;

a first linear actuator and a third linear actuator that are configured to drive the object receptacle along the same linear trajectory; and a controller that is configured to actuate the third linear actuator for taking a section of the object and, after taking the section, to actuate the first linear actuator for positioning the object along the linear trajectory in an observation position of the particle beam apparatus, wherein the movement of the object receptacle for taking the section and the positioning of the object at the observation position are carried out without reversing the direction along the linear trajectory.

* * * * *